(12) United States Patent
Lieber et al.

(10) Patent No.: US 9,595,685 B2
(45) Date of Patent: Mar. 14, 2017

(54) NANOSCALE WIRES, NANOSCALE WIRE FET DEVICES, AND NANOTUBE-ELECTRONIC HYBRID DEVICES FOR SENSING AND OTHER APPLICATIONS

(75) Inventors: Charles M. Lieber, Lexington, MA (US); Xiaojie Duan, Somerville, MA (US); Ruixuan Gao, Cambridge, MA (US); Ping Xie, Needham, MA (US); Xiaocheng Jiang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 285 days.

(21) Appl. No.: 14/124,816

(22) PCT Filed: Jun. 7, 2012

(86) PCT No.: PCT/US2012/041253
§ 371 (c)(1),
(2), (4) Date: Mar. 6, 2014

(87) PCT Pub. No.: WO2012/170630
PCT Pub. Date: Dec. 13, 2012

(65) Prior Publication Data
US 2014/0184196 A1 Jul. 3, 2014

Related U.S. Application Data

(60) Provisional application No. 61/495,919, filed on Jun. 10, 2011.

(51) Int. Cl.
*G01R 1/02* (2006.01)
*H01L 51/05* (2006.01)
(Continued)

(52) U.S. Cl.
CPC .......... *H01L 51/0512* (2013.01); *B82Y 10/00* (2013.01); *B82Y 30/00* (2013.01);
(Continued)

(58) Field of Classification Search
None
See application file for complete search history.

(56) References Cited

U.S. PATENT DOCUMENTS 6,123,819 A    9/2000  Peeters
6,465,331 B1   10/2002 Keeth et al.
(Continued)

FOREIGN PATENT DOCUMENTS

WO    WO 2004/109282 A1   12/2004
WO    WO 2005/059506 A2    6/2005
(Continued)

OTHER PUBLICATIONS

International Preliminary Report on Patentability from International Application No. PCT/US2007/006545 mailed Sep. 25, 2008.
(Continued)

*Primary Examiner* — Jermele M Hollington
(74) *Attorney, Agent, or Firm* — Wolf, Greenfield & Sacks, P.C.

(57) ABSTRACT

The present invention generally relates to nanotechnology, including field effect transistors and other devices used as sensors (for example, for electrophysiological studies), nanotube structures, and applications. Certain aspects of the present invention are generally directed to transistors such as field effect transistors, and other similar devices. In one set of embodiments, a field effect transistor is used where a nanoscale wire, for example, a silicon nanowire, acts as a transistor channel connecting a source electrode to a drain electrode. In some cases, a portion of the transistor channel is exposed to an environment that is to be determined, for (Continued)

example, the interior or cytosol of a cell. A nanotube or other suitable fluidic channel may be extended from the transistor channel into a suitable environment, such as a contained environment within a cell, so that the environment is in electrical communication with the transistor channel via the fluidic channel. In some embodiments, the rest of the transistor channel may be coated, e.g., so that the electrical properties of the transistor channel reflect the electrical behavior of the environment that the fluidic channel is in communication with. Other aspects of the invention are generally directed to methods of making such sensors, methods of using such sensors, kits involving such sensors, or the like.

15 Claims, 15 Drawing Sheets

(51) Int. Cl.
*H01L 51/00* (2006.01)
*G01N 27/414* (2006.01)
*B82Y 40/00* (2011.01)
*B82Y 30/00* (2011.01)
*B82Y 10/00* (2011.01)
*H01L 29/775* (2006.01)
*H01L 29/06* (2006.01)

(52) U.S. Cl.
CPC .......... *B82Y 40/00* (2013.01); *G01N 27/4146* (2013.01); *G01R 1/02* (2013.01); *H01L 51/0002* (2013.01); *H01L 29/0676* (2013.01); *H01L 29/775* (2013.01)

(56) References Cited

U.S. PATENT DOCUMENTS

| | | | |
|---|---|---|---|
| 6,846,654 B1 | 1/2005 | Blackburn et al. | |
| 7,049,625 B2* | 5/2006 | Kern | B82Y 10/00 257/24 |
| 7,129,554 B2 | 10/2006 | Lieber et al. | |
| 7,301,199 B2 | 11/2007 | Lieber et al. | |
| 7,351,313 B2 | 4/2008 | Hasegawa et al. | |
| 7,659,165 B2 | 2/2010 | Koenenkamp | |
| 7,875,480 B2 | 1/2011 | Kamins et al. | |
| 8,319,206 B2* | 11/2012 | Wu | B82Y 10/00 257/40 |
| 8,575,663 B2* | 11/2013 | Lieber | B82Y 15/00 257/253 |
| 9,102,521 B2 | 8/2015 | Lieber et al. | |
| 9,297,796 B2 | 3/2016 | Tian et al. | |
| 2002/0117659 A1 | 8/2002 | Lieber et al. | |
| 2002/0130311 A1 | 9/2002 | Lieber et al. | |
| 2003/0089899 A1 | 5/2003 | Lieber et al. | |
| 2004/0133118 A1 | 7/2004 | Llinas | |
| 2004/0186459 A1 | 9/2004 | Shur et al. | |
| 2004/0264064 A1 | 12/2004 | Sakakima | |
| 2005/0106713 A1 | 5/2005 | Phan et al. | |
| 2005/0133254 A1 | 6/2005 | Tsakalakos | |
| 2005/0224778 A1 | 10/2005 | Dubin et al. | |
| 2005/0241375 A1 | 11/2005 | Naughton | |
| 2005/0253137 A1 | 11/2005 | Whang et al. | |
| 2005/0257821 A1 | 11/2005 | Ramanathan et al. | |
| 2005/0275010 A1 | 12/2005 | Chen et al. | |
| 2006/0006377 A1* | 1/2006 | Golovchenko | B82Y 10/00 257/39 |
| 2006/0054936 A1* | 3/2006 | Lieber | B82Y 10/00 257/210 |
| 2006/0269927 A1 | 11/2006 | Lieber et al. | |
| 2007/0111493 A1 | 5/2007 | Lee et al. | |
| 2007/0264623 A1* | 11/2007 | Wang | B82Y 15/00 435/4 |
| 2008/0149970 A1* | 6/2008 | Thomas | B82Y 10/00 257/288 |
| 2009/0072137 A1* | 3/2009 | Hunt | G01N 23/221 250/305 |
| 2009/0283752 A1* | 11/2009 | Jiang | B82Y 10/00 257/24 |
| 2009/0299213 A1 | 12/2009 | Patolsky et al. | |
| 2010/0006451 A1 | 1/2010 | Gordon et al. | |
| 2010/0022012 A1 | 1/2010 | Lieber et al. | |
| 2010/0151659 A1 | 6/2010 | Hong et al. | |
| 2010/0227382 A1 | 9/2010 | Lieber et al. | |
| 2010/0327894 A1 | 12/2010 | Dang et al. | |
| 2011/0042641 A1 | 2/2011 | Lieber et al. | |
| 2012/0098589 A1* | 4/2012 | Spanier | B82Y 10/00 327/530 |
| 2014/0080139 A1 | 3/2014 | Lieber et al. | |
| 2015/0137794 A1* | 5/2015 | Lieber | G01R 1/30 324/149 |
| 2015/0212039 A1* | 7/2015 | Lieber | B82Y 15/00 435/7.4 |
| 2015/0351691 A1 | 12/2015 | Lieber et al. | |
| 2016/0033498 A1 | 2/2016 | Lieber et al. | |
| 2016/0302682 A1* | 10/2016 | Lieber | A61B 5/685 |

FOREIGN PATENT DOCUMENTS

| | | |
|---|---|---|
| WO | WO 2006/122554 A2 | 11/2006 |
| WO | WO 2006/132659 A2 | 12/2006 |
| WO | WO 2008/027078 A2 | 3/2008 |
| WO | WO 2011/038228 A1 | 3/2011 |
| WO | WO 2014/031709 A1 | 2/2014 |
| WO | WO 2014/043341 A1 | 3/2014 |

OTHER PUBLICATIONS

Canadian Office Action dated Oct. 14, 2014 for Application No. 2,655,340.
European Office Action dated Jan. 29, 2015 for Application No. 07873479.5.
European Office Action dated Jun. 4, 2015 for Application No. 07873479.5.
International Preliminary Report on Patentability from International Application No. PCT/US2013/039228 mailed Nov. 13, 2014.
International Preliminary Report on Patentability from International Application No. PCT/US2013/055910 mailed Mar. 5, 2015.
Office Action mailed Jul. 15, 2014 for U.S. Appl. No. 12/225,142.
Office Action mailed Nov. 25, 2014 for U.S. Appl. No. 12/225,142.
Office Action mailed Jun. 3, 2015 for U.S. Appl. No. 12/225,142.
Office Action mailed Nov. 12, 2015 for U.S. Appl. No. 12/225,142.
Office Action mailed Feb. 23, 2015 for U.S. Appl. No. 14/030,170.
Miscellaneous Office Action mailed Jul. 24, 2015 for U.S. Appl. No. 14/030,170.
Office Action for U.S. Appl. No. 14/030,170 mailed Nov. 3, 2015.
Office Action mailed Jun. 24, 2014 for U.S. Appl. No. 13/497,852.
[No Author Listed] http://www.biologyonline.org/dictionary/In_vitro. Definition of in vitro. Biology-Online Dictionary. Last updated May 16, 2015. Accessed Sep. 2, 2015. 2 pages.
Appell et al., Nanotechnology: Wired for success. Nature. Oct. 10, 2002. 419:553:5.doi:10.1038/419553a.
Duan et al., Intracellular recordings of action potentials by an extracellular nanoscale field-effect transistor. Nat Nanotechnol. Mar. 2012 ;7(3):174-9. Supporting Information included.
Dürkop et al., Extraordinary Mobility in Semiconducting Carbon Nanotubes. Nano Letters. 2004. 4(1):35-9. DOI: 10.1021/nl034841q.
Gabay et al., Engineered self-organization of neural networks using carbon nanotube clusters. Physica A. 2005. 350:611-21. E Pub Nov. 23, 2004.
James et al., Extracellular Recordings From Patterned Neuronal Networks Using Planar Microelectrode Arrays. IEEE Trans. Biomed. Eng. Sep. 9, 2004. 51: 1640-8.
Léonard et al., Novel Length Scales in Nanotube Devices. The American Physical Society. Physical Review Letters. Dec. 13, 1999. 83 (24): 5174-7.

(56) References Cited

OTHER PUBLICATIONS

Lovat et al., Carbon Nanotube Substrates Boost Neuronal Electrical Signaling. Nano Letters. 2005. 5(6). 1107-10.E Pub May, 6 2005. DOI: 10.1021/nl050637m.
Merz et al., Silicon Chip Interfaced with a Geometrically Defined Net of Snail Neurons. Adv Funct Mater. May 2005. 15(5): 739-44. E Pub Apr. 26, 2005. DOI: 10.1002/adfm.200400316.
Offenhausser et al., Field-Effect transistor array for monitoring electrical activity from mammalian neurons in culture. Biosensors & Bioelectronics. Jul. 1, 1997. 12(8): 819-26.
Ramanathan et al., Individually Addressable Conducting Polymer Nanowires Array. Nano Letters. 2004. 4(7): 1237-9.
Rotkin, Theory of Nanotube Devices: From Quantum Models to Novel Effects to New Applications. Applied Physics of Carbon Nanotubes NanoScience and Technology 2005, pp. 1-39. DOI: 10.1007/3-540-28075-8_1.
Sekhar et al., Selective growth of silica nanowires in silicon catalysed by Pt thin film. Nanotechnology. 2006. 17: 4606-13. doi:10.1088/0957-4484/17/18/013.
Sun et al., Finite-size effects in nickel nanowire arrays. Rapid Communications. Physical Review B. Mar. 1, 2000. 61 (10): 4 pages.
Suryavanshi et al., Electrochemical fountain pen nanofabrication of vertically grown platinum nanowires. Nanotechnology. 2007. 18: 105305 (4 pages). doi:10.1088/0957-4484/18/10/105305.
Tanner et al., High-Q GaN nanowire resonators and oscillators. Applied Physics Letters. 2007. 91: 203117.
Tans et al., Individual single-wall carbon nanotubes as quantum wires. Nature. Apr. 3, 1997. 386: 474-7. doi:10.1038/386474a0.
Timko et al., Electronic interface between nanowires and neurons. Abstract. MRS: Materials Research Society. Symposium P-Session P8: Poster Session: Semiconductor Nanowires-Fabrication, Properties and Devices. P8.23. 2006 MRS Spring Meeting & Exhibit. Apr. 18-21, 2006. San Francisco, California. Presented Apr. 19, 2006. 30 pages.
Voelker et al., Signal Transmission from Individual Mammalian Nerve Cell to Field-Effect Transistor. Small. 2005. 1: 206-10. E Pub Dec. 13, 2004. DOI: 10.1002/smll.200400077.
Office Action mailed Apr. 8, 2016 for U.S. Appl. No. 12/225,142.
Office Action mailed Feb. 25, 2016 for U.S. Appl. No. 14/396,542.
Office Action mailed Aug. 10, 2016 for U.S. Appl. No. 14/396,542.
International Search Report and Written Opinion from International Application No. PCT/US2016/025493 mailed Jun. 23, 2016.
Gao et al., General strategy for biodetection in high ionic strength solutions using transistor-based nanoelectronic sensors. Nano Lett. Feb. 9, 2015;15:2143-48.
U.S. Appl. No. 12/225,142, filed Mar. 11, 2009, Patolsky et al.
U.S. Appl. No. 14/396,542, filed Oct. 23, 2014, Lieber et al.
U.S. Appl. No. 12/308,207, filed Dec. 16, 2009, Lieber et al.
U.S. Appl. No. 14/030,170, filed Sep. 18, 2013, Lieber et al.
U.S. Appl. No. 13/497,852, filed Jul. 2, 2012, Tian et al.
U.S. Appl. No. 14/788,134, filed Jun. 30, 2015, Lieber et al.
U.S. Appl. No. 14/030,170, filed Sep. 18, 2013, Gao et al.
International Search Report and Written Opinion from International Application No. PCT/US2007/006545 mailed Apr. 10, 2008.
International Search Report and Written Opinion from International Application No. PCT/US2012/041253 mailed Dec. 26, 2012.
International Preliminary Report on Patentability from International Application No. PCT/US2012/041253 mailed Dec. 27, 2013.
Advisory Action mailed May 22, 2014 for U.S. Appl. No. 13/497,852.
Cohen-Karni et al., Graphene and nanowire transistors for cellular interfaces and electrical recording. Nano Lett. Mar. 10, 2010;10(3):1098-102.
Fromherz, "Electrical interfacing of nerve cells and semiconductor chips" Chemphyschem—A European Journal of Chemical Physics & Physical Chemistry, Wiley VCH, Weinheim, DE, vol. 3, No. 3, Mar. 12, 2002 pp. 276-284, XP002300227.
Fromherz, "Semiconductor chips with ion channels, nerve cells and brain" Physica E—Low-Dimensional Systems and Nanostructures, Elsevier Science BV, NL, vol. 16, No. 1, Jan. 2003, pp. 24-34, XP002300226.
Kong et al., Nanotube molecular wires as chemical sensors. Science. Jan. 28, 2000;287:622-5.
Patolsky et al. "Detection, stimulation, and inhibition of neuronal signals with high-density nanowire transistor arrays" Science, vol. 313, Jun. 25, 2006, pp. 1100-1105, XP002474456.
Qing et al., "Nanowire transistor arrays for mapping neural circuits in acute brain slices," PNAS, vol. 107, No. 5, pp. 1882-1887 (Feb. 2, 2010).
Final Office Action mailed Dec. 4, 2014 for U.S. Appl. No. 13/497,852.
[No Author Listed] http://www.circuitstoday.com/fetapplications. FET applications: Circuit Board Design. Circuits Today. Aug. 31, 2009. 10pgs. Accessed Sep. 2, 2015.
[No Author Listed] http://www.merriamwebster.com/dictionary/in%20vitro. Definition of in vitro. Merriam-Webster. 2015 Merriam-Webster, Incorporated. Accessed Sep. 2, 2015. 4 pages.
[No Author Listed] http://www.mycircuits9.com/2012/05/applicationsoffieldeffect.html. Applications of Field Effect Transistors (FET): Electronic Circuit Boards. My Circuits 9. Accessed Sep. 2, 2015. 3 pages.
[No Author Listed] http://www.thefreedictionary.com/in+vitro. Definition of in vitro. The Free Dictionary. English-Spanish Medical Dictionary. Copyright 2006. The McGraw-Hill Companies, Inc. Accessed Sep. 2, 2015. 2 pages.
[No Author Listed] https://en.wikipedia.org/wiki/Fieldeffect_transistor. Definition of Field-effect transistor (FET). Wikipedia, the free encyclopedia. Last Updated Aug. 31, 2015. Accessed Sep. 2, 2015. 8 pages.
[No Author Listed] https://en.wikipedia.org/wiki/In_vitro. Definition of in vitro. Wikipedia, the free encyclopedia. Last Updated Aug. 13, 2015. Accessed Sep. 2, 2015. 5 pages.
[No Author Listed] https://en.wikipedia.org/wiki/Logic_gate. Definition of Logic Gate. Wikipedia, the free encyclopedia. Last Updated Aug. 9, 2015. Accessed Sep. 2, 2015. 9 pages.
[No Author Listed] https://www.google.com/?gws_rd=ssl#q=in+vitro+definition. Definition of invitro. Google Search. Accessed Sep. 2, 2015. 2pgs.
[No Author Listed] Molecular Wire. Wikipedia®:the Free Encyclopedia. Wikimedia Foundation, Inc. Mar. 11, 2015. Accessed Apr. 30, 2015.
Appell et al., Nanotechnology: Wired for success. Nature. Oct. 10, 2002. 419: 553:5.doi:10.1038/419553a.
Biercuk et al., Topics Applied Physics: Electrical Transport in Single-Wall Carbon Nanotubes. Carbon Nanotubes: Advanced Topics in the Synthesis, Structure, Properties and Applications. 2008. 111:455-93. DOI: 10.1007/978-3-540-72865-8_15.
Bradley et al., Integration of Cell Membranes and Nanotube Transistors. Nano Letters. Mar. 23, 2005. 5: 841-5. E Publication Mar. 31, 2005. DOI: 10.1021/nl050157v.
Bulashevich et al., Nanotube Devices: A Microscopic Model. JETP Letters. 2002. 75 (4): 205-9.
Calarco et al. Size-dependent Photoconductivity in MBE-Grown GaN-Nanowires. Nano Letters. 2005. 5(5): 981-4.
Dekker, Carbon Nanotubes as Molecular Quantum Wires. Physics Today. May 1999. 52(5):22-28. doi: 10.1063/1.882658.
Duan et al., Intracellular recordings of action potentials by an extracellular nanoscale field-effect transistor. Nat Nanotechnol. Mar. 2012;7(3):174-9. Supporting Information included.

\* cited by examiner

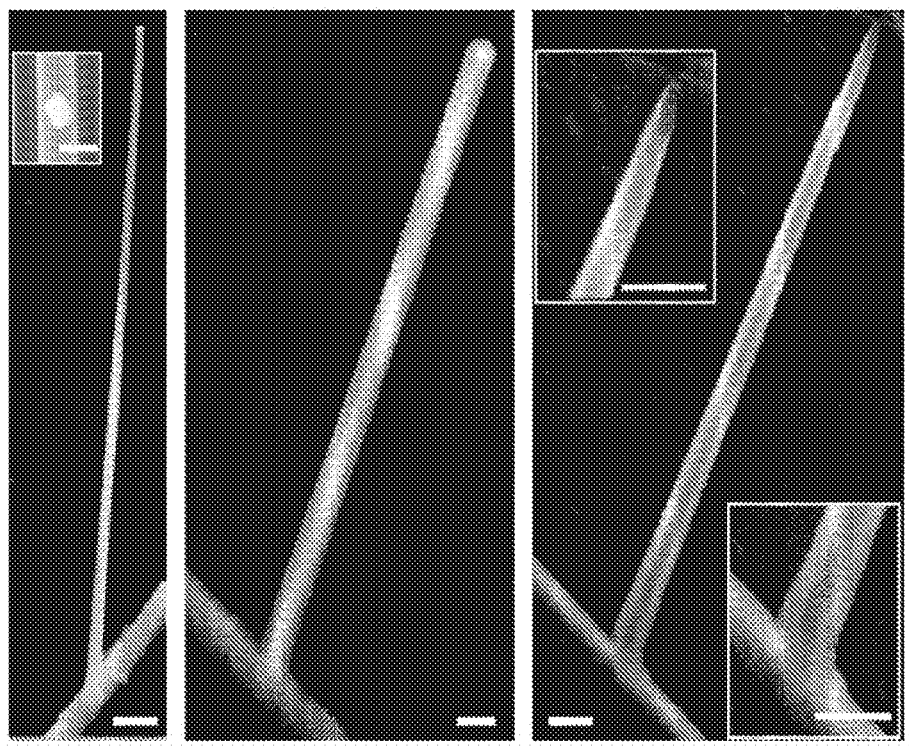

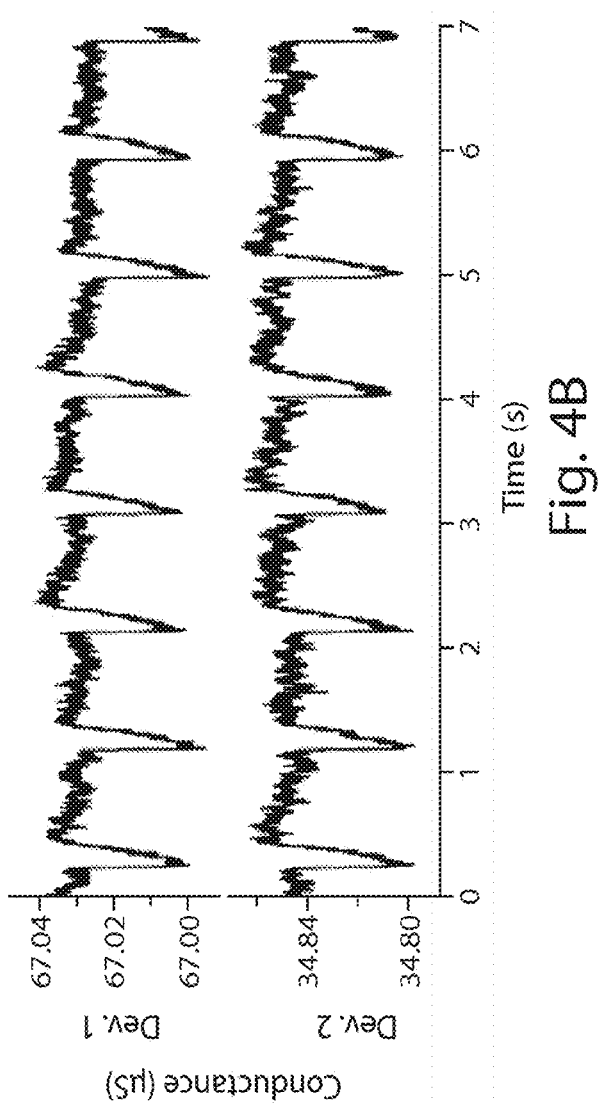
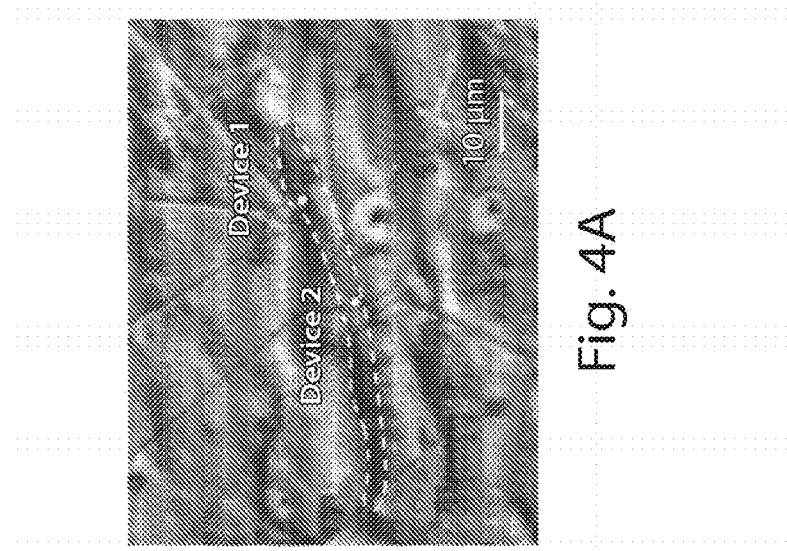
Fig. 4B
Fig. 4A

NANOSCALE WIRES, NANOSCALE WIRE FET DEVICES, AND NANOTUBE-ELECTRONIC HYBRID DEVICES FOR SENSING AND OTHER APPLICATIONS

RELATED APPLICATIONS

This application is a national phase filing under 35 U.S.C §371 of International Application No. PCT/US2012/041253, filed Jun. 7, 2012, entitled "Nanoscale Wires, Nanoscale Wire FET Devices, and Nanotube-Electronic Hybrid Devices For Sensing and Other Applications," which claims the benefit of U.S. Provisional Patent Application Ser. No. 61/495,919, filed Jun. 10, 2011, entitled "Nanoscale Wires, Nanoscale Wire FET Devices, and Nanotube-Electronic Hybrid Devices for Sensing and Other Applications," by Lieber, et al., each of which is incorporated herein by reference.

GOVERNMENT FUNDING

This invention was made with government support under Grant No. 5DP1OD003900 awarded by the National Institutes of Health. The government has certain rights in the invention.

FIELD OF INVENTION

The present invention generally relates to nanotechnology, including field effect transistors and other devices used as sensors (for example, for electrophysiological studies), nanotube structures, and other applications.

BACKGROUND

Interest in nanotechnology, in particular sub-microelectronic technologies such as semiconductor quantum dots and nanoscale wires, has been motivated by the challenges of chemistry and physics at the nanoscale, and by the prospect of utilizing these structures in electronic and related devices. Nanoscale articles might be well-suited for transport of charge carriers and excitons (e.g. electrons, electron pairs, etc.) and thus may be useful as building blocks in nanoscale electronics applications. Nanoscale wires are well-suited for efficient transport of charge carriers and excitons, and thus are expected to be important building blocks for nanoscale electronics and optoelectronics.

SUMMARY OF THE INVENTION

The present invention generally relates to nanotechnology, including field effect transistors and other devices used as sensors (for example, for electrophysiological studies), nanotube structures, and other applications. The subject matter of the present invention involves, in some cases, interrelated products, alternative solutions to a particular problem, and/or a plurality of different uses of one or more systems and/or articles.

In one aspect, the present invention is generally directed to a field effect transistor. In one set of embodiments, the field effect transistor includes a source electrode, a drain electrode, a transistor channel electrically connecting the source electrode to the drain electrode, and a nanotube positioned such that one end of the nanotube physically contacts a side of the transistor channel.

According to another set of embodiments, the field effect transistor includes a source electrode, a drain electrode, a transistor channel electrically connecting the source electrode to the drain electrode, and a fluidic channel in electrical communication with a portion of the transistor channel and a contained environment.

In another set of embodiments, the field effect transistor comprises a source electrode, a drain electrode, and a transistor channel, for example, a nanoscale wire, electrically connecting the source electrode to the drain electrode. In some cases, the nanoscale wire comprises a core and a shell substantially coating the core except at one location.

In another set of embodiments, the article comprises a nanoscale wire, and a nanotube positioned such that one end of the nanotube physically contacts a side of the nanoscale wire. In some embodiments, the article comprises a transistor, wherein the transistor comprises the nanoscale wire. For example, the nanoscale wire may be present in a transistor channel within the transistor. In certain cases, the transistor is a field effect transistor.

In yet another set of embodiments, the article includes a first electrode positioned externally of a cell, a second electrode positioned externally of the cell, and an electrical connector electrically connecting the first electrode to the second electrode, wherein the electrical connector is in fluidic communication with the interior of a cell. In some embodiments, the electrical connector comprises a nanowire. In certain cases, the first electrode, the second electrode, and the electrical connector together define a field effect transistor. In some instances, the article further comprises a fluidic channel connecting the electrical connector to the interior of a cell.

The article, in still another set of embodiments, includes a substrate comprising a plurality of field effect transistors. In some cases, a plurality of the field effect transistors each comprise a nanotube disposed substantially perpendicularly relative to a substrate.

According to still another set of embodiments, the article includes a plurality of cells in electrical communication with each other. In some embodiments, at least two of the cells each have at least partially inserted therein a nanotube. In certain instances, each of the nanotubes is in electrical communication with electrical recording device.

In one set of embodiments, the article includes a cell, and a nanoscale wire external of the cell, where the nanoscale wire is in fluid communication with cytosol of the cell. In yet another set of embodiments, the article includes a contained environment, and a nanoscale wire external of the contained environment, where the nanoscale wire is in fluid communication with the contained environment.

In another aspect, the present invention is generally directed to a method. According to one set of embodiments, the method includes acts of providing a first nanoscale wire, growing a second nanoscale wire in contact with the first nanoscale wire, coating the first nanoscale wire and/or the second nanoscale wire with a coating material, and removing at least a portion of the second nanoscale wire.

The method, in accordance with another set of embodiments, includes acts of providing a plurality of cells, at least some of which each have at least partially inserted therein a nanotube in fluid communication with a field effect transistor external of the cells, exposing the plurality of cells to a drug suspected of being able to alter electrical communication of the cells, and determining a change in an electrical property of at least some of the cells via the field effect transistors.

In another set of embodiments, the method includes acts of providing a nanotube immobilized relative to a nanowire, and inserting at least a portion of the nanotube into a cell without inserting the nanowire into the cell.

In one set of embodiments, the method includes an act of applying a substantially nonconductive coating material to a branched nanoscale wire.

The method, in another set of embodiments, includes acts of providing a branched nanoscale wire comprising a first portion having a first composition and a second portion having a second composition; and etching away the second portion of the branched nanoscale wire without etching away the first portion.

According to still another set of embodiments, the method includes acts of providing a branched nanoscale wire comprising a first portion having a first composition and a second portion comprising a carbon nanotube, and heating the branched nanoscale wire to remove the carbon nanotube without removing the first portion.

In accordance with yet another set of embodiments, the method includes acts of providing a nanoscale wire, blocking a plurality of discrete locations on the first nanoscale wire with a blocking material, coating the nanoscale wire with a substantially nonconductive coating material, and etching away the blocking material from the nanoscale wire, thereby producing a nanoscale wire coated with the coated material except at plurality of discrete locations.

In one set of embodiments, the method is a method of determining an electrical property of a cell. In certain embodiments, the method comprises acts of inserting a fluidic channel into an interior of a cell, wherein the fluidic channel is in electrical communication with a portion of a transistor channel of a field effect transistor and the transistor channel is external of the cell, and determining an electrical property of the cell.

In another aspect, the present invention encompasses methods of making one or more of the embodiments described herein, for example, a transistor such as a field effect transistor as discussed herein. In still another aspect, the present invention encompasses methods of using one or more of the embodiments described herein, for example, a transistor such as a field effect transistor as discussed herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1E illustrate sensors in accordance with one set of embodiments of the invention;

FIGS. 4A-4D illustrate monitoring of cells using a plurality of sensors, in yet other embodiments of the invention;

DETAILED DESCRIPTION

The present invention generally relates to nanotechnology, including field effect transistors and other devices used as sensors (for example, for electrophysiological studies), nanotube structures, and applications. Certain aspects of the present invention are generally directed to transistors such as field effect transistors, and other similar devices. In one set of embodiments, a field effect transistor is used where a nanoscale wire, for example, a silicon nanowire, acts as a transistor channel connecting a source electrode to a drain electrode. In some cases, a portion of the transistor channel is exposed to an environment that is to be determined, for example, the interior or cytosol of a cell. A nanotube or other suitable fluidic channel may be extended from the transistor channel into a suitable environment, such as a contained environment within a cell, so that the environment is in electrical communication with the transistor channel via the fluidic channel. In some embodiments, the rest of the transistor channel may be coated, e.g., so that the electrical properties of the transistor channel reflect the electrical behavior of the environment that the fluidic channel is in communication with. Other aspects of the invention are generally directed to methods of making such sensors, methods of using such sensors, kits involving such sensors, or the like.

Thus, one aspect of the invention is generally directed to sensors including transistors such as field effect transistors, or other suitable devices, for detecting a condition within an environment that is external to the sensor. In some cases, the environment may be one that is contained, for example, inside an interface. For instance, the environment may be an environment contained within an emulsion droplet, a micelle, a liposome, a cell, or the like. In some cases, the contained environment may have a volume of less than about 1 ml, less than about 100 microliters, less than about 10 microliters, less than about 1 microliter, less than about 100 nanoliters, less than about 10 nanoliters, or less than about 1 nanoliter. As discussed herein, the sensor may include one or more fluidic channels that can be introduced to the environment external to the sensor such that the sensor is in electrical, chemical, and/or physical communication with the environment. In some cases, the environment is a contained environment that is the fluidic channel is in communication with, although the contained environment may not physically contact other components of the sensor. Thus, for example, a cell may be contained in an extracellular fluid, and a sensor may be positioned such that the fluidic channel is in communication with the cytosol within the cell (i.e., the contained environment), while the rest of the sensor is in physical contact only with the extracellular fluid and/or the plasma membrane that defines the "interface" or external boundary of the cell.

Figure 1A:
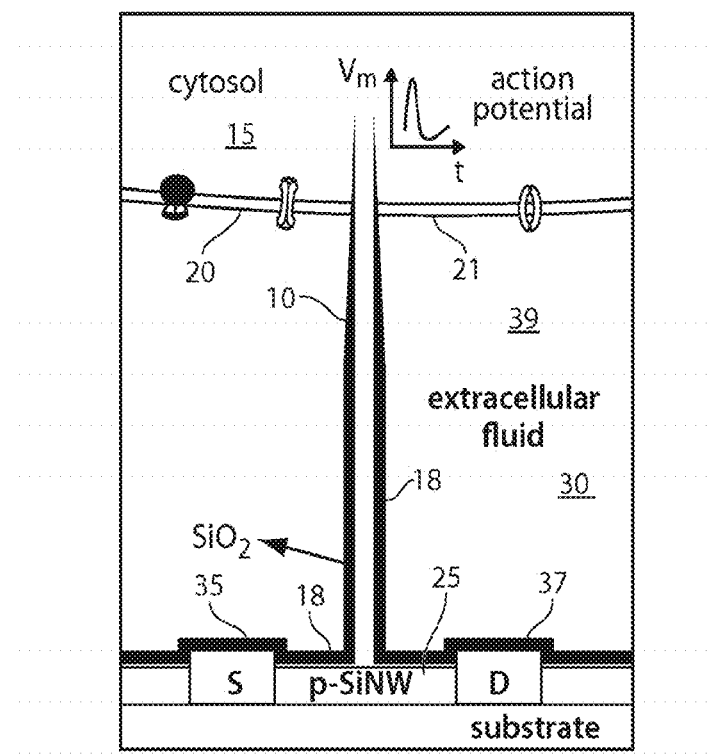

As a specific non-limiting example, referring now to FIG. 1A, a sensor in accordance with one set of embodiments of the invention is now described. In this figure, a field effect transistor 30 is formed from source electrode 35, drain electrode 37, and transistor channel 25 connecting the source electrode 35 to drain electrode 37. Although a field effect transistor is shown here, this is by way of example only, and in other embodiments, other transistors or other suitable devices may also be used, as discussed below. In this figure, transistor channel 25 is formed from a p-doped silicon nanowire ("SiNW"). Other nanoscale wires may be used in other embodiments, however, although a silicon nanowire is shown here as an illustrative example.

Connected to a portion of transistor channel 25 is nanotube 10, which functions as a fluidic channel in this example. Fluid from an environment to be sensed, for example, cytosol (intracellular fluid) 15 within cell 20 may be able to at least partially enter nanotube 10 and in some cases, come into contact with a portion of transistor channel 25. In this way, transistor channel 25 is in electrical, chemical, and/or physical communication with cytosol 15 in the interior of cell 20. Thus, the interior of cell 20 (i.e., the cytosol) defines a contained environment that is in contact with field effect transistor 30 via nanotube 10.

It should be noted here that the other components of field effect transistor 30, such as source electrode 35, drain electrode 37, and other portions of transistor channel 25, do not directly physically contact cytosol 15 in the interior of cell 20, although these components are in contact with extracellular fluid 39 in this example. In other embodiments, some or all of these components may also come into contact with the plasma membrane 21 of cell 20, although even then, these components would not come into contact with cytosol 15 in the interior of cell 20. Accordingly, as shown in this example, the sensor is able to communicate with an environment that is contained inside an interface via a fluidic channel.

To prevent extracellular fluid 39 from adversely interacting with field effect transistor 30, coating material 18 ($SiO_2$ in this example) is used. For instance, coating material 18 may be positioned on transistor channel 25 such that transistor channel 25 can be controlled by electrical, chemical, and/or physical interactions with the contained environment, e.g., with cytosol 15, instead of electrical, chemical, and/or physical interactions with extracellular fluid 39. For example, coating material 18 may be chosen to be substantially nonconductive, and/or coating material 18 may be substantially chemically inert relative to extracellular fluid 39, such that substantially no chemical reactions or physical interactions between extracellular fluid 39 and transistor channel 25 can occur that could affect the functioning of transistor channel 25. In some cases, such as is shown here, a fluidic channel extending into cytosol 15 in the interior of cell 20 may be defined by a nanotube 10 formed, at least in part, out of the coating material, e.g., so that extracellular fluid 39 does not have any substantial electrical, chemical, and/or physical interactions with the interior of nanotube 10.

As previously noted, the illustration discussed with respect to FIG. 1A is by way of example only, and in other embodiments, other environments, such as contained environments, may be sensed using a sensor as discussed herein. Thus, for instance, a fluidic channel of the sensor may be inserted into a first, contained environment that is surrounded by a second environment. For instance, a contained environment may be defined as the interior of a cell, an emulsion droplet, a micelle, a liposome, etc., while the second, surrounding environment may be any fluid separate from and containing the containing environment, for example, water, an aqueous fluid, an organic fluid or the like.

In addition, as mentioned, the sensor in FIG. 1A was illustrated using a field effect transistor. However, in other aspects of the invention, other transistors, or other devices, may be used instead of a field effect transistor. For instance, a sensor or other apparatus may include a transistor such as a bipolar junction transistor or a metal electrode. As another example, a nanotube or other fluidic channel may be fabricated as part of an electrode or a logic gate, which can be used as a sensor or other apparatus as discussed herein. The sensor may be used to determine a suitable environment, such as a contained environment. For example, the sensor or other apparatus may be placed in electrical, chemical, and/or physical communication with the environment, such that an appropriate electrical, chemical, and/or physical property can be determined by a sensor and/or so that an electrical, chemical, or other physical property may be affected by an apparatus. "Determine," as used herein, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction.

Non-limiting examples of suitable electrical properties that may be determined or altered include charge, conductance, impedance, resistance, voltage (e.g., with respect to fluid externally of the cell, ground, etc.), current, potential, or the like. As another example, a recognition entity to an analyte suspected of being contained in the environment may be placed in the sensor, e.g., so that the sensor is able to determine the analyte within the solution, for example, through changes in electrical properties. Additional details are discussed below, as well as in U.S. Pat. No. 7,129,554, issued Oct. 31, 2006, entitled "Nanosensors," by Lieber, et al., incorporated herein by reference in its entirety.

In one set of embodiments, a field effect transistor may be used in the sensor or other apparatus. The field effect transistor can include a source electrode, a drain electrode, and an electrical connector, such as a nanoscale wire, electrically connecting the source electrode to the drain electrode. The electrical connector may thus act as a transistor channel within the field effect transistor, and may be formed from any suitable material able to electrically connect the source electrode to the drain electrode. The electrical connector may be, for example, a nanoscale wire or a larger wire, for instance, an electrical line, a microscale wire, a planar substrate, graphene, or the like. The electrical connector may be embedded in a substrate, or free-standing in some embodiments. In one set of embodiments, the electrical connector may be substantially cylindrical.

If a sensor or other apparatus includes an electrode, for example, containing a fluidic channel or as part of a transistor such as a field effect transistor, the electrodes may be formed out of any suitable material. If more than one electrode is present, the electrodes may be formed out of the same or different materials. Typically, the electrodes are formed from metals (e.g., deposited on a surface using known techniques, such as photolithography). Non-limiting examples of suitable electrode materials include silicon, or metals such as gold, silver, copper, zinc, cadmium, iron, nickel, cobalt, palladium, platinum, etc.

In one set of embodiments, the electrical connector includes a nanoscale wire. The nanoscale wire may include one or more nanowires or nanotubes. Typically, nanowires are solid while nanotubes are hollow, as discussed below. The nanoscale wire may be formed out of any suitable electrically conductive material, for example, a carbon nanotube, a semiconductor nanowire, a ZnO nanowire, graphene (e.g., a graphene ribbon), a metal nanowire, or the like, and may have any suitable dimensions. Other examples of suitable materials are discussed in detail below.

In some cases, a nanoscale wire within the sensor or other apparatus (e.g., a nanowire and/or a nanotube) may have an average cross-sectional diameter of less than about 5 micrometers and/or a length of less than about 1 micrometer. For example, the nanoscale wire may have a cross-sectional diameter of less than about 5 micrometers, less than about 3 micrometers, less than about 1 micrometer, less than about 800 nm, less than about 600 nm, less than about 400 nm, less than about 200 nm, less than about 100 nm, less than about 80 nm, less than about 60 nm, less than about 40 nm, less than about 20 nm, less than about 10 nm, or less than about 5 nm. In some cases, the diameter may be at least about 2 nm, at least about 5 nm, at least about 10 nm, at least about 20 nm, or at least about 50 nm. In a nanotube, the inner diameter or the outer diameter may have any of these dimensions, and these dimensions may be independently chosen. As a specific non-limiting example, the nanotube may have an inner diameter of 50 nm and an outer diameter of 150 nm.

In some cases, the nanoscale wire may have a length of at least about 10 nm, at least about 30 nm, at least 50 nm, at least about 100 nm, at least about 300 nm, at least about 500 nm, at least about 1 micrometer, at least about 3 micrometers, at least about 5 micrometers, at least about 10 micrometers, at least about 30 micrometers, at least about 50 micrometers, at least about 100 micrometers, at least about 300 micrometers, at least about 500 micrometers, or at least about 1 mm. In some instances, the nanoscale wire may have a length of less than about 1 micrometer, less than about 800 nm, less than about 600 nm, less than about 400 nm, less than about 200 nm, or less than about 100 nm. In one set of embodiments, a sensor or other apparatus comprising the nanoscale wire(s) may have maximum dimensions no greater than the ones described in this paragraph.

In some embodiments, an apparatus is used to deliver a current or a potential to an environment such as a contained environment, and in certain embodiments, a sensor is used to determine an electrical, chemical, and/or physical property of the environment. In some cases, the same device may be used to both determine and alter an environment.

For example, in one set of embodiments, a sensor or other apparatus may be used that may be able to determine and/or apply an (absolute) electric potential of greater than about 0.1 microvolts, greater than about 1 microvolt, greater than about 10 microvolts, greater than about 100 microvolts, greater than about 1 millivolt, greater than about 10 millivolts, greater than about 100 millivolts, greater than about 1 volt, or even greater. In some embodiments, the nanoscale wire may detect an electric potential between about 0.1 microvolts and 1 volt, between about 0.1 microvolts and about 100 microvolts, between about 10 microvolts and about 10 millivolts, or between about 1 millivolt and about 1 volt. The potential may be positive or negative. As specific examples, the intracellular potential of a cell may be held to be between about −40 millivolts and −100 millivolts, between about −60 millivolts and −90 millivolts, between about −50 millivolts and −80 millivolts, or between about −40 millivolts and −60 millivolts, etc. In another set of embodiments, the nanoscale wire may determine and/or apply a current greater than about 0.1 picoamps, greater than about 1 picoamp, greater than about 10 picoamps, greater than about 100 picoamps, greater than about 1 nanoamp, greater than about 10 nanoamps, greater than about 100 nanoamps, greater than about 1 microamp, greater than about 10 microamps, greater than about 100 microamps, greater than about 1 milliamp, greater than about 10 milliamps, greater than about 100 milliamps, greater than about 1 amp, or even more. In some embodiments, the nanoscale wire transmit a current between about 0.1 picoamps and about 100 microamps, between about 0.1 picoamps and about 100 picoamps, between about 10 picoamps and about 10 nanoamps, between about 1 nanoamp and 1 microamp, or between about 100 nanoamps and about 100 microamps.

As mentioned, in the case of a field effect transistor, the nanoscale wire may, in some embodiments, perform as a transistor channel in the transistor. The nanoscale wire may allow, for example, an increase or decrease in the flow of current between the source and drain of the transistor in response to a threshold electrical potential, e.g., as is controlled via interaction with the nanoscale wire and a fluid within the fluidic channel. The interaction may be, e.g., an electrical, chemical, and/or physical interaction. The threshold electrical potential may be within any of the voltage ranges listed above.

In one set of embodiments, there may be one or more fluidic channels in physical contact with the nanoscale wire, e.g., with an end or a side of the nanoscale wire. Thus, fluid within the fluidic channel may be able to access at least a portion of the nanoscale wire, e.g., causing an electrical, chemical, and/or physical interaction with the nanoscale wire. For instance, as previously discussed, this interaction may allow the nanoscale wire to function as a transistor channel in a field effect transistor, or other device as is discussed herein. In some embodiments, the fluidic channel is defined by one or more nanotubes (which are hollow), or other structure able to contain a fluid. Examples of such structures include, without limitation, a microfluidic chamber, a microfluidic channel, a structure having a bowl shape, or the like. In the case of a nanotube, the nanotube may be positioned such that one end of the nanotube is closed by the nanoscale wire. A non-limiting example of such a configuration is shown in FIG. 1A.

The nanotube (or other fluidic channel) may be formed out of any suitable material. For instance, the fluidic channel may comprise a conductive material, a non-conductive material, a semiconductive material, or the like, or combinations thereof. It should be noted that, in some embodiments, the nanotube does not need to play a role in any electrical, chemical, and/or physical interactions between the fluid and the nanoscale wire (e.g., a transistor channel for a field effect transistor). Thus, in some cases, the fluidic channel may simply channel fluid between the environment and the nanoscale wire at the bottom of the fluidic channel. Thus, the fluidic channel does not have to be electrically conductive (although it can be in some embodiments), and the fluidic channel may be formed out of any suitable material able to channel a fluid, including non-conductive or semiconductive materials, as well as conductive materials.

For example, in one set of embodiments, the nanotube may have an electrical conductivity less than that of a semiconductive carbon nanotube having substantially the same dimensions as the nanotube. Non-limiting examples of suitable materials that the fluidic channel can comprise include oxides such as metal oxides (for example, $SiO_2$, $Al_2O_3$, $TiO_2$, $HfO_2$, $ZnO_2$, etc.); metals (e.g., Au, Pt, Cu, Ag, etc.), or the like. In one embodiment, however, the fluidic channel may include one or more carbon nanotubes. The nanotube may have any of the dimensions for nanotubes described herein.

In some embodiments, a coating material may be present on at least a portion of a fluidic channel and/or a nanoscale wire, e.g., that is used as a transistor channel for a field effect transistor. As discussed, the coating material may be selected to be substantially electrically nonconductive, and/or substantially chemically inert relative to a surrounding environment, e.g., such that substantially no chemical reactions or physical interactions between the surrounding environment and the underlying portions can occur. For example, the coating material may be selected to be substantially electrically nonconductive such that the electrical properties of the nanoscale wire is controlled by the electrical properties of fluid contained within the fluidic channel, rather than the electrical behavior of the environment external of the fluidic channel.

The coating material may be formed out of any suitable material. In some embodiments, the coating material may be have the same composition as the nanotubes described above, although in other embodiments, the coating material may have a different composition. Non-limiting examples of suitable materials that can be used as coating materials include oxides such as metal oxides (for example, $SiO_2$, $Al_2O_3$, $TiO_2$, $HfO_2$, $ZnO_2$, etc.); metals (e.g., Au, Pt, Cu, Ag, etc.), or the like, depending on the application.

A fluidic channel may be positioned to be substantially perpendicular to a nanoscale wire, e.g., as is shown in FIG. 1A for a nanotube. However, in other embodiments of the invention, the fluidic channel need not be positioned at a right angle, and can be positioned at any other suitable angle. For instance, discussed in detail below are techniques for forming nanoscale structures comprising a nanotube and a nanoscale wire at any suitable angle. The angle of the fluidic channel with respect to the underlying nanoscale wire (and/or other electrical connector) may be, for example, at least about 30°, at least about 45°, at least about 60°, at least about 65°, at least about 70°, at least about 75°, at least about 80°, or at least about 85°, etc.

In some embodiments, the field effect transistor (or other apparatus) may be positioned on the surface of a substrate, for example, of a chip, such as a silicon wafer. One example is a planar CMOS chip. In some cases, for example, the chip may include one or more sensors or other apparatuses such as those discussed herein, and the sensors or other apparatuses may be positioned on the surface of the substrate using various techniques for semiconductor device fabrication known to those of ordinary skill in the art, for example, photolithography, ion implantation, etching, chemical vapor deposition, physical vapor deposition, molecular beam epitaxy, or the like. Any number of sensors and/or other apparatuses may be present, and they may each be independently the same or different. In some cases, for instance, a plurality of sensors and/or other apparatuses may be used for determining a cell or a plurality of cells, or other applications such as those discussed herein. For example, there may be 1, 2, 3, 5, 10, 15, 30, 45, 60, 100, 300, 1000, or more sensors and/or other apparatuses present on the substrate. In some cases, the nanoscale wires may be positioned on (or formed in the substrate), with some or all of the nanotubes (or other fluidic channels) positioned substantially perpendicularly relative to the substrate, or at other angles such as those described above.

According to certain aspects of the invention, sensors and/or other apparatuses such as those described herein may be prepared by preparing a branched nanoscale wire, coating the branched nanoscale wire with a coating material, and etching a portion of the coating material and/or the branched nanoscale wire to form a fluidic channel. In some cases, the branched nanoscale wire may be heterogeneous, for instance, defining a first portion susceptible to etching and a second portion that is relatively more resistant to etching (although some etching may still occur, at least in certain embodiments). In other embodiments, however, other methods may be used to form a sensor and/or other apparatus. For example, a nanotube, such as a carbon nanotube, may be grown from a substrate surface or a nanoscale wire, e.g., using atomic layer deposition, chemical vapor deposition, physical vapor deposition, water-assisted chemical vapor deposition, or the like. Other fluidic channels, such as microfluidic chambers or microfluidic channels, may also be grown, e.g., using techniques such as photolithography, bulk or surface micromachining, replication techniques (embossing, printing, casting and injection molding), nuclear track or chemical etching, etc.

Figures 5A, 5B, 5C:
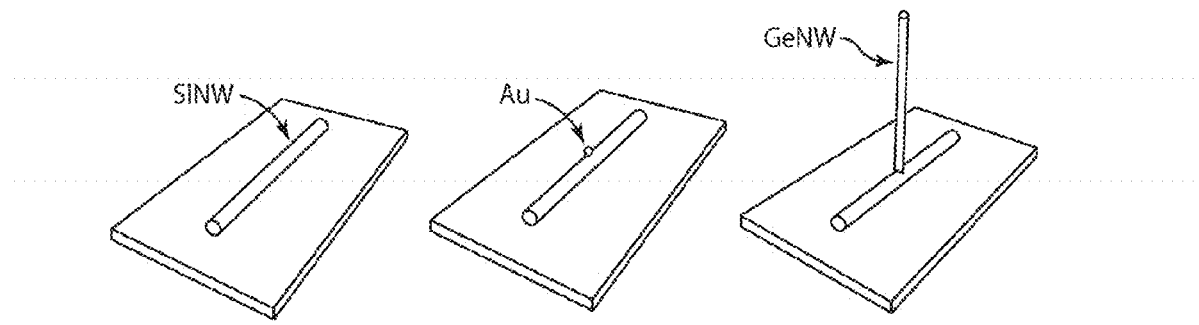
FIGS. 5A-5I schematically illustrate the fabrication of a sensor in accordance with one embodiment of the invention.
Figures 5D, 5E, 5F:
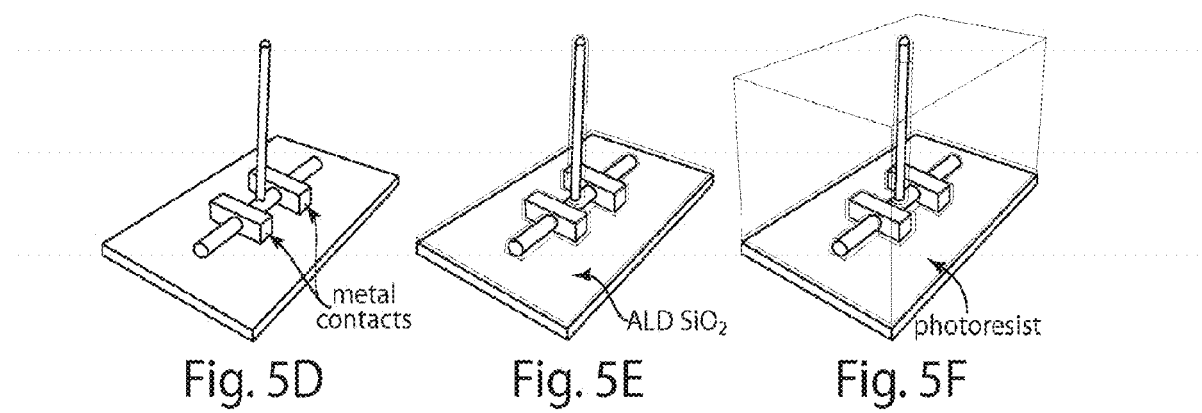

One non-limiting example of this process is now discussed with reference to FIG. 5. FIG. 5A illustrates a SiNW deposited on the surface of a substrate (e.g., a chip), and FIG. 5B shows the positioning of a gold nanoparticle on a specific location on the SiNW. It should be understood that SiNW and gold are discussed here as non-limiting examples; as discussed elsewhere herein, other materials may also be used instead of and/or in addition to SiNW or gold. In FIG. 5C, a germanium nanowire ("GeNW") is grown to be substantially perpendicular to the SiNW, using the nanoparticles to facilitate this reaction, as discussed herein. Next, in FIG. 5D, metal contacts are deposited or defined on the substrate, e.g., as source and drain electrodes, then the entire structure is coated with a coating material, for example, $SiO_2$. One technique that can be used for coating is atomic layer deposition ("ALD"). A photoresist may be added to cover the substrate and the structures thereon such that only a portion of the GeNW remains above the surface of the photoresist. Next, the photoresist can be exposed to an etchant (e.g., buffered hydrofluoric acid) to remove the portion of the coating material above the surface of the photoresist. The photoresist and the GeNW may then be removed by exposure to one or more suitable etchants, e.g., photoresist remover and hydrogen peroxide ($H_2O_2$). Substantially all of the GeNW can be removed, thereby leaving behind a hollow nanotube structure, which can define a fluidic channel that contacts the original SiNW. As mentioned, use of these materials with respect to FIG. 5 is solely by way of example, and in other embodiments, other materials and/or techniques may be used, e.g., as discussed herein.

For example, in one set of embodiments, a first nanoscale wire is provided and a second nanoscale wire is grown to be in contact with the first nanoscale wire, e.g., using techniques such as those discussed herein. Each of the nanoscale wires may independently be, for example, a solid nanowire, a nanotube, etc., as discussed herein. The contact may be, for example, end-on (e.g., forming a "T" structure, as is shown in FIG. 1), and the angle of contact may be 90° or any other angle discussed herein. In some embodiments, however, the contact need not be end-on. As a specific example, the nanoscale wires may cross at their middles (e.g., forming an "X" structure").

Any suitable technique for growing the second nanoscale wire to be in contact with the first nanoscale wire may be used. In some cases, the second nanoscale wire is first grown, then brought to be in contact with the first nanoscale wire; in other embodiments, however, the second nanoscale wire may be directly grown from the first nanoscale wire. Non-limiting examples of techniques for growing the first nanoscale wire and/or the second nanoscale wire include vapor-liquid-solid growth techniques, laser assisted catalytic growth, catalytic chemical vapor deposition, solution based growth, chemical vapor deposition, or the like. Further techniques may be seen, for example, in U.S. patent application Ser. No. 09/935,776, filed Aug. 22, 2001, entitled "Doped Elongated Semiconductors, Growing Such Semiconductors, Devices Including Such Semiconductors, and Fabricating Such Devices," by Lieber, et al., published as U.S. Patent Application Publication No. 2002/0130311 on Sep. 19, 2002, or U.S. patent application Ser. No. 10/196,337, filed Jul. 16, 2002, entitled "Nanoscale Wires and Related Devices," by Lieber, et al., published as U.S. Patent Application Publication No. 2003/0089899 on May 15, 2003, each incorporated herein by reference. Although gold nanoparticles were used in the discussion above with respect to FIG. 5, this is by way of example only. If a catalyst is used, any catalyst able to catalyze the production of nanoscale wires may be used, depending on the technique used to produce the nanoscale wire, e.g., as catalyst nanoparticles. A wide range of materials may be used as the catalyst nanoparticle in these embodiments, for example, a transition metal such as gold, silver, copper, zinc, cadmium, iron, nickel, cobalt, palladium, platinum, aluminum, or the like.

After growth, the first nanoscale wire and/or the second nanoscale wire may be coated with a coating material, using any suitable technique known to those of ordinary skill in the art for coating, for example, via atomic layer deposition, chemical vapor deposition, physical vapor deposition, casting, or the like. Any coating material may be used, for instance, oxides such as metal oxides (for example, $SiO_2$, $Al_2O_3$, $TiO_2$, $HfO_2$, $ZnO_2$, etc.); metals (e.g., Au, Pt, Cu, Ag, etc.), or the like.

The coating material may be at least partially blocked, for example, by applying a photoresist or another suitable blocking material that can be later removed to the first nanoscale wire and/or the second nanoscale wire. In some cases, as discussed, the photoresist may be applied to substantially cover the first nanoscale wire and/or the second nanoscale wire. In some cases, the photoresist may be applied such that only the end of the second nanoscale wire is not covered by photoresist. A variety of photoresists known to those of ordinary skill in the art may be used, depending on the application (e.g., poly(methyl methacrylate), poly(methyl glutarimide), phenol formaldehyde resin, SU-8 (Microchem Corp., Newton, Mass.), S1805, S1813, S1818, etc.).

After blockage of the nanoscale wires, e.g., by photoresist or another suitable blocking material, a portion of the coating material, e.g., on the uncovered tip of the second nanoscale wire, may be removed, e.g., using an etchant or other technique able to remove the uncovered portion of the coating material, for example, reactive ion etching. Non-limiting examples of etchants potentially suitable for removing coating materials include HCl, HF, $NH_4F$ or the like, and may be readily selected by those of ordinary skill in the art based on the selection of the coating material.

Next, the photoresist or another suitable blocking material may also be removed, e.g., by using etching, or another suitable removal technique. In some embodiments, an etchant may etch the photoresist while not substantially etching the coating material, e.g., such that sufficient coating material remains to coat the first nanoscale wire and/or form a nanotube or other fluidic channel after exposure to the etchant. Thus, the photoresist may be substantially completely removed by the etchant, while only a portion of the coating material is removed.

The second nanoscale wire may also be removed, e.g., by etching or another suitable technique. The etchant may be chosen to be able to remove the second nanoscale wire without substantially etching away other components of the device, and may be selected based on the choice of materials used for the device by those of ordinary skill in the art. As a specific non-limiting example, if the second nanoscale wire comprises a carbon nanotube, then the second nanoscale wire may be removed, for example, by heating the device to drive off the carbon nanotube, e.g., as $CO_2$. Examples of etchants that may be used in the above include, but are not limited to e.g., $H_2O_2$, KOH, $I_2$/KI, ethylene diamine and pyrocatechol, iron chloride, plasmas such as $CCl_4$ or $CF_4$ plasma, tetramethylammonium hydroxide, or the like.

As discussed, branched nanoscale wires are used in accordance with certain aspects of the invention. See, e.g., U.S. patent application Ser. No. 12/310,764, filed Mar. 6, 2009, entitled "Branched Nanoscale Wires," by Lieber, et al., published as U.S. Patent Application Publication No. 2011/0042641 on Feb. 24, 2011, incorporated herein by reference in its entirety. In some embodiments, nanoparticles, such as gold nanoparticles, are deposited onto a nanoscale wire, and then segments or "branches" are grown from the nanoparticles. The nanoscale wire may be, for example, a semiconductor nanoscale wire, a nanoscale wire having a core and a shell, etc. In one embodiment, for instance, gold nanoparticles are deposited onto the nanoscale wire by etching the nanoscale wire using, for example, HF, to produce an H-terminated surface. Without wishing to be bound by any theory, it is generally believed that the H-terminated surface, in certain cases, causes the electrochemical reduction of gold ions in solution, for example, from a charged state (e.g., $Au^{2+}$ or $Au^{3+}$) to a neutral (i.e., $Au^0$) state, i.e., such that the gold ions precipitate out of solution to form nanoparticles on the surface of the H-terminated surface. The size of the deposited gold nanoparticles may be controlled, for instance, by controlling the concentration of gold in solution, and/or by controlling the deposition or exposure time.

Typically, only one nanoparticle is attached to the surface of a nanoscale wire, and the nanoparticle may be used as a blocking material to block coating of the nanoscale wire with the coating material at that particular location. In some (but not all) embodiments, the location may then be used to grow a nanoscale wire thereon, e.g., as discussed herein. However, in certain embodiments, two, three, four, or more nanoparticles may be attached to the surface of a nanoscale wire, e.g., to produce a device having a nanoscale wire and a plurality of nanotubes. In some cases, some or all of the nanotubes may be positioned such that one end of the nanotube physically contacts a side of the nanoscale wire. In other embodiments, however, the nanotubes may contact the nanoscale wire in other ways, e.g., contacting at their middles.

After deposition of the nanoparticles, segments of material may be grown from them, e.g., to form a nanowire. In some cases, CVD (chemical vapor deposition) or other various vapor-liquid-solid (VLS) growth techniques may be used to grow the segments of material, for example, to produce segments comprising semiconductors such as Si, GaAs, GaP, InP, CdSe, ZnSe, CdS, ZnS, etc. In some embodiments, however, solution-phase synthesis techniques may be used. For instance, gold segments may be grown from nanoparticles by annealing the nanowire/nanoparticle composite and exposing the nanoparticles to a solution containing gold (for example, gold tetrachloride acid, $HAuCl_4$). Without wishing to be bound by any theory, it is believed that deposition of the gold is constrained due to the presence of surfactants. Surfactants such as cetyl trimethyl ammonium bromide (CTAB) may preferentially interact with the {100} and {111} facets of the gold nanoparticle, and thus, growth occurs primarily along the <110> direction, causing uniaxial elongation.

Thus, using such techniques, branched nanoscale wires having at least first segment having a first composition and a second segment having a second composition different from the first composition may be produced. As discussed herein, in certain embodiments, the second segment may be formed to be a sacrificial template that is to be removed, e.g., by etching, heating, laser ablation, etc.

In some embodiments, one or more of the segments of the branched nanoscale wire comprises a semiconductor, for example, a Group IV semiconductor, a Group III-V semiconductor, a Group II-VI semiconductor, or the like. Examples include, but are not limited to, Si, GaAs, GaP, InP, CdSe, ZnSe, CdS, ZnS, etc. If more than one segment comprising a semiconductor is present, the segments may each independently be the same or different. As a non-limiting example, if one segment is Si, another segment within the branched nano scale wire may be GaAs, GaP, InP, CdSe, ZnSe, CdS, and/or ZnS. Combinations of these and/or other semiconductors are also possible, for example, a branched nanoscale wire may have three or more types of semiconductors, such as Si/GaAs/GaP, Si/GaAs/InP, etc.

In one set of embodiments, one or more nanoparticles may be deposited onto a nanoscale wire by producing a charge on the nanoscale wire, and exposing the charged nanoscale wire to at least one nanoparticle having an opposite charge to the charged nanoscale wire. The nanoscale wire may be, for example, a semiconductor nanoscale wire, a nanoscale wire having a core and a shell, a branched nanoscale wire (e.g., produced as described herein), etc. The charge on the nanoscale wire may be produced, for instance, electrically, by immobilizing a charged entity to the nanoscale wire, etc. As a non-limiting example, if metal nanoparticles such as gold nanoparticles are used, which often have a negative charge, then a positively-charged entity may first be immobilized to the nanoscale wire. The positively-charged entity can be, for instance, a positively-charged polymer such as poly(lysine), poly(ethyleneimine), or poly(allylamine hydrochloride). The nanoparticles can then be attracted to the positively-charged entity and thereby become adsorbed onto the nanoscale wire. As discussed herein, segments can then be grown from the nanoparticles to produce a branched nanoscale wire.

In another set of embodiments, a surface of the nanoscale wire is treated to produce a reducing surface, i.e., a surface that can reduce a positive ion, and the reducing surface is then exposed to an ionic solution, whereby an ion in solution can be reduced by the reducing surface. If the ions are reduced to a 0 state, the ions may precipitate out of solution, e.g., forming nanoparticles on the reducing surface of the nanoscale wire. The reducing surface can be prepared, for example, by etching the nanoscale wire with an etching solution. An example of an etching solution is HF, which causes the surface to become H-terminated. Other examples include $NH_4F$ or $NH_4F/HF$. Exposure of the H-terminated surface to positively-charged metal ions in solution can cause the reduction of the metal ions ultimately to a zero charge, which may thus cause precipitation of the metal ions from solution, e.g., to form nanoparticles. Typically, the metal is more electronegative than hydrogen. As an example, gold ions in solution (e.g., $Au^{3+}$ or $Au^{2+}$) can become reduced to $Au^0$ to form gold nanoparticles. A non-limiting example of a solution containing gold ions is gold tetrachloride acid, $HAuCl_4$. As another example, silver ions in solution (e.g., $Ag^+$) can become reduced to $Ag^0$ to form silver nanoparticles. A non-limiting example of a solution containing silver ions is $AgNO_3$. Further non-limiting examples of suitable metals include Pd, Pt, or Cu. The size and/or density of the deposited nanoparticles may be controlled by, e.g., the concentration of metal ions in solution, and/or the exposure time.

Next, additional segments (e.g., comprising a semiconductor and/or a metal) can then be grown from the nanoparticles to produce a branched nanoscale wire. In one set of embodiments, semiconductor segments can be grown from the nanoparticles using conventional techniques such as CVD (chemical vapor deposition) or other various vapor-liquid-solid (VLS) growth techniques. See, e.g., Wang, et al., "Rational Growth of Branched and Hyperbranched Nanowire Structures," *Nano Lett.*, 4(5):871-874 (2004), which discusses growth of branched nanowire structures produced using vapor-liquid-solid (VLS) growth techniques. See also U.S. patent application Ser. No. 09/935,776, filed Aug. 22, 2001, entitled "Doped Elongated Semiconductors, Growing Such Semiconductors, Devices Including Such Semiconductors, and Fabricating Such Devices," by Lieber, et al., published as U.S. Patent Application Publication No. 2002/0130311 on Sep. 19, 2002, or U.S. patent application Ser. No. 10/196,337, filed Jul. 16, 2002, entitled "Nanoscale Wires and Related Devices," by Lieber, et al., published as U.S. Patent Application Publication No. 2003/0089899 on May 15, 2003, each incorporated herein by reference.

For instance, certain arrangements may utilize metal-catalyzed CVD techniques ("chemical vapor deposition") to synthesize segments. CVD synthetic procedures can readily be carried out by those of ordinary skill in the art. The segments may also be grown through laser catalytic growth. If uniform diameter nanoparticles (less than 10% to 20% variation depending on how uniform the nanoparticles are) are used as the catalytic cluster, segments with uniform size (diameter) distribution can be produced, where the diameter of the segments is determined by the size of the nanoparticles. By controlling growth time, segments with different lengths can be grown.

One technique that may be used to grow the segments is catalytic chemical vapor deposition ("C-CVD"). In C-CVD, reactant molecules are formed from the vapor phase. Nanoscale wires may be doped by introducing the doping element into the vapor phase reactant (e.g. diborane and phosphane). The doping concentration may be controlled by controlling the relative amount of the doping compound introduced in the composite target. The final doping concentration or ratios are not necessarily the same as the vapor-phase concentration or ratios. By controlling growth conditions, such as temperature, pressure or the like, segments having the same doping concentration may be produced.

Other techniques to produce segments are also contemplated. For example, nanoscale wires of any of a variety of materials may be grown directly from vapor phase through a vapor-solid process. In yet another set of embodiments, metal segments can be grown in a solution-phase synthesis technique from the nanoparticles, by exposing the nanoparticles to a solution containing a metal ion. The metal ion may be the same or different than the metal in the nanoparticles. For certain types of nanoparticles, deposition of the metal ions on the nanoparticle can be constrained due to the presence of surfactants or other species that preferentially interact with certain faces of the nanoparticle, and thus, growth in certain directions may be preferred. For instance, if the nanoparticle is gold, deposition of gold onto the nanoparticle may be constrained and growth along the <110> axis of the deposited gold nanoparticle may be preferred, leading to uniaxial elongation. As a specific non-limiting example, a surfactant such as cetyl trimethyl ammonium bromide (CTAB) may preferentially interact with the {100} and {111} facets of a gold nanoparticle, causing growth to occur primarily along the <110> axis. The diameter and/or the aspect ratio may be controlled by controlling, for example, the concentration of metal ion in solution, and/or the acidity or pH, i.e., the hydrogen ion concentration. Examples of metals that can be used include, but are not limited to, noble metals such as gold, silver, copper, zinc, cadmium, iron, nickel, cobalt, palladium, platinum, or the like.

As discussed, in certain aspects of the invention, a sensor may be used to determine environments such as contained environments, e.g., an environment contained inside an interface. An interface may divide a contained environment from a surrounding environment. The interface may, in some embodiments, be defined as a specific material, for example, by an amphiphilic material (e.g., a phospholipid or a surfactant). In some embodiments, the interface is a lipid bilayer. In another example, however, an interface may be defined as a phase boundary between two substantially immiscible phases; for example, the interface may be formed by oil-water mixture, such as in an emulsion.

The environment to be determined by the sensor may be a contained environment contained within an emulsion, a fluidic droplet, a micelle, a liposome, a cell (such as an electrogenic cell, i.e., one that exhibits electrical activity, such as a neuron or a cardiac cell), or any entity having an interface that is able to define an internal contained environment. If a cell is used, the cell may be an isolated cell or may be part of a group of cells, such as in a tissue or biofilm. The cell may be any suitable cell, e.g., a human cell, an animal cell, a non-human mammalian cell, a bacterial cell, a eukaryotic cell, or an archaeal cell. Non-limiting examples of cells include neurons, cardiomyocytes, muscle cells, and pancreatic beta cells. The surrounding environment that surrounds the contained environment may include, for example, a liquid (e.g., cytosol, water, an aqueous fluid, an organic fluid, etc.) and/or a gas, and can be readily chosen or determined by those of ordinary skill in the art.

A nanoscale wire or other electrical connector in contact with an interface may be used to communicate with the interior environment contained by the interface. The communication, may be, e.g., electrical, chemical, and/or physical communication. In some cases, the nanoscale wire or other electrical connector may be capable of sending and/or receiving an electrical current, and/or passing an electrical current through the nanoscale wire and through a fluidic channel into the contained environment. In certain embodiments, the contained environment may be probed to determine a property, such as an electrical property, of the contained environment. For instance, a sensor may be used to determine an electrical property of the contained environment. The sensor may, in some embodiments, determine an electrical property, such as conductance, charge, impedance, resistance, voltage (e.g., with respect to fluid externally of the cell, ground, etc.), current, potential, or the like in the contained environment.

In some embodiments, the sensor may be used to determine other properties of the contained environment, for example, a chemical, and/or physical in the contained environment. For example, an electrical property of the sensor may be correlated with a chemical, and/or physical property within the contained environment. As a specific non-limiting example, the signal corresponding to a first property (i.e., electrical potential or electrical current) may be correlated with a second property. For example, the electrical potential determined by a sensor may be correlated with pH, concentration of an analyte, ionic concentration, fluid viscosity, or the like. In some embodiments, a reaction entity can be used, e.g., contained within a surface of the fluidic channel, such as on a nanotube wall and/or on a nanoscale wire or other electrical connector, and interaction between a binding partner (for example, an analyte) and the reaction entity may produce a determinable change in an electrical property of the electrical connector, which can be determined to determine a chemical, and/or physical in the contained environment.

In certain embodiments, a nanotube or other fluidic channel may be used to directly access the contained environment, while other portions of the device do not come into physical contact with the contained environment. For example, a fluid within the contained environment may come into physical contact with a nanoscale wire within a device (e.g., a transistor channel) via a fluidic channel such that the nanoscale wire is in electrical communication with the fluid. Other portions of the nanoscale wire or the device (e.g., the electrodes) may not come into direct physical contact with the fluid within the contained environment. Such a device can be used, for example, as a sensor to sense an electrical state of the contained environment, to apply an electrical signal to the contained environment, or the like.

The fluidic channel may be inserted into the contained environment using any suitable technique, e.g., mechanically (for example, using a micromanipulator or a micropipette). In some embodiments, the fluidic channel is inserted using mechanical force. For instance, the fluidic channel and/or the interface may be manipulated such that the fluidic channel and the interface are brought into contact. For example, a cell may be manipulated, e.g., using a micromanipulator or a micropipette, and brought into contact with the fluidic channel. One of ordinary skill in the art would recognize that such a method requires an input of energy (e.g., applying a force to an object such that the object displaces along a vector). However, in some embodiments, substantially less energy may be required for a fluidic channel to be inserted through the interface. For instance, in some cases, relatively favorable chemical interactions may occur between the fluidic channel and the interface defining the contained environment.

In one set of embodiments, for instance, a fluidic channel may be treated, i.e., chemically, to facilitate entry through the interface into the contained environment. For example, in some embodiments, a fluidic channel may spontaneously penetrate the interface defining the contained environment, e.g., due to a material present on at least a portion of the fluidic channel. Non-limiting examples of such materials include amphiphilic materials include phospholipids, such as phosphatidate, phosphatidylethanolamine, phosphatidylcholine, phosphatidylserine, phosphatidylinositol, phosphatidylinositol phosphate, phosphatidylinositol bisphosphate, and phosphatidylinositol triphosphate, surfactants, polymers, proteins, and polysaccharides. In some cases, the material may be coupled to the fluidic channel using functional cross-linkers, such as homobifunctional cross-linkers, comprising homobifunctional NHS esters, homobifunctional imidoesters, homobifunctional sulfhydryl-reactive linkers, difluorobenzene derivatives, homobifunctional photoactive linkers, homobifunctional aldehyde, bis-epoxides, homobifunctional hydarzide etc.; heterobifuntional cross-linkers; or trifuntional cross-linkers, or the like.

Thus, in one set of embodiments, a fluidic channel may be capable of interacting (e.g., chemically) with an interface, e.g., defining a contained environment, such as in a cell, liposome, or the like. For example, a fluidic channel may contact the interface and fuse with a portion of the interface. As used in this context, "fuse" means that the nanotube integrates into the interface (e.g., a lipid bilayer) such that the lipid bilayer (or other interface) forms a continuous phase around one or more portions of the fluidic channel. In some embodiments, the lipid bilayer or other interface may rearrange around at least a portion of the fluidic channel, thereby allowing entry of the fluidic channel to occur into the contained environment.

In some embodiments, when a fluidic channel interacts with an interface, a portion of the fluidic channel may extend completely through the interface. As a non-limiting example, a nanotube may penetrate a cell membrane such that a portion of the nanotube is in contact with the cytosol (or intracellular fluid) inside of the cell. In certain embodiments, a nanotube or other fluidic channel may penetrate more than one interface, e.g., more than one lipid bilayer. For example, a nanotube may penetrate the cell membrane of a cell and another membrane inside the cell (e.g., the membrane of an organelle), or a fluidic channel may be used to penetrate a double emulsion droplet, etc. In one set of embodiments, cells may be cultured near the nanotubes, and in some cases, the cells may spontaneously uptake at least a portion of the nanotube.

Devices such as those described herein may be used in a variety of applications, in accordance with some aspects of the invention. Non-limiting examples of applications include the study of cells, e.g., electrogenic cells, or the screening of drugs or other agents by exposing the drugs or other agents to a plurality of cells, and determining differences in a property (e.g., an electrical, chemical, and/or physical property) of at least some of the cells in response to the drug or other agents. In certain embodiments, the drug or other agent may be one that is drug that is suspected of being able to alter a property, such as an electrical property, of a cell. For instance, the drug (or other agent) may be suspected of being able to alter electrical communication between a plurality of cells, as is discussed below. As a specific non-limiting example, an assay may be performed where cells are treated with one or more drugs or other agents (e.g., a library of drug candidates), and the effect of the agent, alone or in combination with other agents, known drugs (i.e., pharmaceutical agent), or the like on an electrical, chemical, and/or physical property of a cell may be determined.

In some embodiments of the invention, an apparatus may be used to stimulate a response in a contained environment, and/or to communicate with at least a portion of the contained environment. The interaction may be, for instance, electrical, chemical, and/or physical. For example, an electrical stimulus, such as current or voltage, may be applied using an apparatus, through the fluidic channel, into the contained environment, or a chemical may be released from the apparatus through the fluidic channel into the contained environment. In some embodiments, for example, the application of an electrical stimulus to a cell, e.g., current and/or voltage, may induce an action potential within the cell.

As a specific non-limiting example, in certain instances, the apparatus may be used to determine electrical activity in a cell. For instance, the apparatus may be used in certain embodiments instead of (or in addition to) a patch clamp and/or voltage clamp. In one set of embodiments, a plurality of such apparatuses as disclosed herein may be used, e.g., to determine an electrical property of a cell (or other contained environment) at more than one location within the cell, and/or to determine an electrical property of a network of cells. For example, certain embodiments of the invention are generally directed to substrates comprising a plurality of such apparatuses (e.g., on a substrate), which may be used for various applications such as multiplex assays. For example, a plurality of suitable apparatuses can be used to assay a plurality of cells, e.g., essentially simultaneously. In another example, a plurality of apparatuses may be used to assay a plurality of regions of a cell, e.g., essentially simultaneously. Such an assay may be advantageous for determining, for example, how electrical potential inside a cell varies between a first region and a second region. The cells may be isolated and/or networked such that the cells are in electrical communication, e.g., via gap junctions or the like. In some embodiments, a substrate may contain one or more devices as described herein, and cells may be exposed to the substrate, or cultured on the substrate in certain cases. The plurality of devices may interface with the cells, for example such that two, there, or more cells have at least partially inserted therein a fluidic channel, such as a nanotube. In some embodiments, for instance, a plurality of apparatuses may be in electrical communication with one or more electrical recording devices, e.g., so that the cells (or network of cells) may be analyzed, e.g., to determine an electrical, chemical, and/or physical property of the cell (or other contained environment).

The present invention, in various aspects, includes nanoscale wires, each of which can be any nanoscale wire, including nanorods, nanowires, nanotubes, nanoribbons, or the like. In some cases, the present invention may also include larger components, e.g., not necessarily of nanoscale dimensions, although the components may have the same compositions as the nanoscale wires disclosed herein. For example, a transistor may include an electrical connector that has a cross-sectional diameter of several micrometers, and the electrical connector may comprise any of the materials disclosed below, or elsewhere herein.

The nanoscale wires (or other electrical connector) may be formed of any suitable material, for example, organic and inorganic conductive and semiconducting polymers, semiconductor components or pathways and the like. Other conductive or semiconducting elements that may be used in some instances include, for example, inorganic structures such as Group IV, Group III/Group V, Group II/Group VI elements, transition group elements, or the like, as described below. For example, the nanoscale wire or other electrical connector may be made of semiconducting materials such as silicon, indium phosphide, gallium nitride, graphene, and others. The nanoscale wires or other electrical connector may also include, for example, any organic, inorganic molecules that are polarizable or have multiple charge states.

The nanoscale wire or other electrical connector may include various materials, including metals, semiconductors, and optionally dopants. For example, nanoscale wires or other electrical connectors may include main group and metal atom-based wire-like silicon, transition metal-containing wires, gallium arsenide, gallium nitride, indium phosphide, germanium, and/or cadmium selenide. Other examples include metals such as gold, silver, copper, zinc, cadmium, iron, nickel, cobalt, palladium, platinum, etc.

The following are non-comprehensive examples of materials that may be used as dopants or nanoscale wires (or other electrical connectors). For example, the dopant or the nanoscale wire (or other electrical connector) may be an elemental semiconductor, for example, silicon, germanium, tin, selenium, tellurium, boron, diamond, graphene, or phosphorous. The dopant or the nanoscale wire (or other electrical connector) may also be a solid solution of various elemental semiconductors. Examples include a mixture of boron and carbon, a mixture of boron and $P(BP_6)$, a mixture of boron and silicon, a mixture of silicon and carbon, a mixture of silicon and germanium, a mixture of silicon and tin, or a mixture of germanium and tin.

In some embodiments, the dopant or the nanoscale wire (or other electrical connector) may include mixtures of Group IV elements, for example, a mixture of silicon and carbon, or a mixture of silicon and germanium. In other embodiments, dopant or the nanoscale wire (or other electrical connector) may include a mixture of a Group III and a Group V element, for example, BN, BP, BAs, AlN, AlP, AlAs, AlSb, GaN, GaP, GaAs, GaSb, InN, InP, InAs, or InSb. Mixtures of these may also be used, for example, a mixture of BN/BP/BAs, or BN/AlP. In other embodiments, dopant or the nanoscale wire (or other electrical connector) may include alloys of Group III and Group V elements. For example, the alloys may include a mixture of AlGaN, GaPAs, InPAs, GaInN, AlGaInN, GaInAsP, or the like. In other embodiments, the dopant or the nanoscale wire (or other electrical connector) may also include a mixture of Group II and Group VI semiconductors. For example, the semiconductor may include ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, (ZnCd)Se, or Zn(SSe), or the like. Additionally, alloys of different groups may also be possible, for example, a combination of a Group II-Group VI and a Group III-Group V semiconductor, for example, $(GaAs)_x(ZnS)_{1-x}$. Other examples of dopants or nanoscale wires (or other electrical connectors) may include combinations of Group IV and Group VI elements, such as GeS, GeSe, GeTe, SnS, SnSe, SnTe, PbO, PbS, PbSe, or PbTe. Other semiconductor mixtures may include a combination of a Group I and a Group VII, such as CuF, CuCl, CuBr, CuI, AgF, AgCl, AgBr, AgI, or the like. Other compounds may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al,Ga,In)_2(S,Se,Te)_3$, $Al_2CO$, $(Cu,Ag)(Al,Ga,In,Tl,Fe)(S,Se,Te)_2$ and the like.

For Group IV dopant materials, a p-type dopant may be selected from Group III, and an n-type dopant may be selected from Group V, for example. For silicon semiconductor materials, a p-type dopant may be selected from the group consisting of B, Al and In, and an n-type dopant may be selected from the group consisting of P, As and Sb. For Group III-Group V semiconductor materials, a p-type dopant may be selected from Group II, including Mg, Zn, Cd and Hg, or Group IV, including C and Si. An n-type dopant may be selected from the group consisting of Si, Ge, Sn, S, Se and Te. It will be understood that the invention is not limited to these dopants, but may include other elements, alloys, or materials as well.

Controlled doping of nanoscale wires or other electrical connectors can be carried out to form, e.g., n-type or p-type semiconductors. One set of embodiments involves use of at least one semiconductor, controllably-doped with a dopant (e.g., boron, aluminum, phosphorous, arsenic, etc.) selected according to whether an n-type or p-type semiconductor is desired. A bulk-doped semiconductor may include various combinations of materials, including other semiconductors and dopants. For instance, the nanoscale wire (or other electrical connector) may be a semiconductor that is doped with an appropriate dopant to create an n-type or p-type semiconductor, as desired. As one example, silicon may be doped with boron, aluminum, phosphorous, or arsenic. In various embodiments, this invention involves controlled doping of semiconductors selected from among indium phosphide, gallium arsenide, gallium nitride, cadmium selenide. Dopants including, but not limited to, zinc, cadmium, or magnesium can be used to form p-type semiconductors in this set of embodiments, and dopants including, but not limited to, tellurium, sulfur, selenium, or germanium can be used as dopants to form n-type semiconductors from these materials. These materials may define direct band gap semiconductor materials and these and doped silicon are well known to those of ordinary skill in the art. The present invention contemplates use of any doped silicon or direct band gap semiconductor materials for a variety of uses.

Certain aspects of the invention are generally directed to fabricating semiconductor nanoscale wires and other nanoscale objects (or other electrical connectors) such as those described herein. Techniques useful for fabricating nanoscale wires or other electrical connectors include, but are not limited to, vapor phase reactions (e.g., chemical vapor deposition ("CVD") techniques such as metal-catalyzed CVD techniques, catalytic chemical vapor deposition ("C-CVD") techniques, organometallic vapor phase deposition-MOCVD techniques, atomic layer deposition, chemical beam epitaxy, etc.), solution phase reactions (e.g., hydrothermal reactions, solvothermal reactions), physical deposition methods (e.g., thermal evaporation, electron-beam evaporation, laser ablation, molecular beam epitaxy), vapor-liquid-solid ("VLS") growth techniques, laser catalytic growth ("LCG") techniques, surface-controlled chemical reactions, or the like, for instance, as disclosed in Ser. No. 10/196,337, entitled, "Nanoscale Wires and Related Devices," filed Jul. 16, 2002, published as Publication No. 2003/0089899 on May 15, 2003, incorporated herein by reference. The nanoscale wires or other electrical connectors may be either grown in place or deposited after growth. For instance, the nanoscale wires or other electrical connectors may be grown on a substrate using techniques such as photolithography, e.g., using conventional photolithography, submicron photolithography, extreme-UV lithography or nanoimprint lithography.

In certain embodiments, a nanoscale wire containing one or more kinks can be grown using certain vapor-liquid-solid ("VLS") growth techniques. For instance, in one set of embodiments, a catalyst particle may be used to grow a first portion of a nanoscale wire, for instance, by exposing the catalyst particle to a first reactant, such as a gaseous reactant. Such a wire may be axially extended in a first direction.

Exposure of the catalyst particle to the first reactant may then be stopped, which may stop axial growth of the wire. The catalyst particle can then be perturbed and/or supersaturated to restart growth of the wire. For instance, the catalyst particle may be exposed to exposed to a second reactant (which may be the same or different than the first reactant) and supersaturated and/or nucleated to restart nanoscale wire growth. In some cases, the direction of growth of the nanoscale wire may be altered, for example, by altering the direction of flow of the second reactant, relative to the first reactant.

In some embodiments, the nanoscale wire may be doped during growth of the wire, and in certain cases, the dopant may be changed, e.g., added or removed, and/or the concentration of the dopant may be changed, and/or the dopant may be removed and a second dopant added, etc. Thus, as a non-limiting example, the growing nanoscale wire may be exposed to a first dopant in the first reactant and to a second dopant in the second reactant to create a semiconductor nanoscale wire having a first portion having a first doping characteristic, and a second portion having a second doping characteristic, e.g., as previously described.

This process may also be repeated as many times as desired to grow nanoscale wires having any suitable number of kinks. In addition, the length of each of the substantially straight segments may be controlled, for example, by controlling the length of time the nanoscale wire is exposed to a reactant. In some embodiments, the angle of the kink may be controlled by the crystallographic orientation of the nanoscale wire, e.g., such that an angle of about 120° is created at the kink region, as described above.

As mentioned, certain nanoscale wires may be grown using a vapor-liquid-solid (VLS) mechanism. One feature of the VLS growth process is that equilibrium phase diagrams can be used to select catalysts and growth conditions, and thereby enable rational synthesis of nanoscale wire materials. Semiconductor nanoscale wires of the III-V materials GaAs, GaP, GaAsP, InAs, InP and InAsP, the II-VI materials ZnS, ZnSe, CdS and CdSe, and IV-IV alloys of SiGe can be synthesized in high yield and purity using VLS techniques. Other semiconductors, such as GaAs and CdSe, can also be grown. The nanoscale wires may be prepared as single crystals with dimensions such as those described herein.

Generally, the size of the nanoscale wire is controlled, at least in part, by the size of the catalyst particle used to grow the nanoscale wire. The catalyst particle may be prepared using any suitable technique, for example, using the LCG method, which uses laser ablation to generate nanometer diameter catalytic clusters or particles. This methodology allows the direct formation of adjacent regions having different compositions within a nanoscale wire, such as a p/n junction, and/or adjacent regions differing in concentration of a particular element or composition. In these techniques, a nanoparticle catalyst is used during growth of the nanoscale wire, which may be further subjected to different semiconductor reagents during growth. Alteration of the semiconductor reagents may allow for the formation of abrupt or gradual changes in the composition of the growing semiconductor material, allowing heterostructured materials to be synthesized.

Techniques for doping after growth of the nanoscale wires may also be used, in addition to (or instead of) doping during growth. For example, a nanoscale wire such as those described herein may be first synthesized, then doped post-synthetically with various dopants as discussed herein. For example, a p/n junction can be created by introducing p-type and n-type dopants on a single nanoscale wire. The p/n junction can then be further annealed to allow the dopants to migrate further into the nanoscale wire to form a bulk-doped nanoscale wire.

As mentioned, the nanoscale wire may be doped during growth of the nanoscale wire. Doping the nanoscale wire during growth may result in the property that the doped nanoscale wire is bulk-doped. Furthermore, such doped nanoscale wires may be controllably doped, such that a concentration of a dopant within the doped nanoscale wire can be controlled and therefore reproduced consistently, making possible the commercial production of such nanoscale wires. Additionally, the dopant may be systematically altered during the growth of the nanoscale wire, for example, so that the final nanoscale wire has a first doped region comprising a first dopant and a second doped region differing in composition from the first region, for example, by comprising a second dopant, comprising the first dopant at a different concentration, or omitting the first dopant.

In some embodiments, dopants may be introduced during vapor phase growth of nanoscale wires. For instance, laser vaporization of a composite target composed of a desired material (e.g. silicon or indium phosphide) and/or a catalytic material (e.g. gold) may create a hot, dense vapor. The vapor may condense into liquid nanoclusters through collision with a buffer gas. Growth may begin when the liquid nanoclusters become supersaturated with the desired phase and can continue as long as reactant is available. Growth may terminate when the nanoscale wire passes out of the hot reaction zone or when the temperature is decreased.

Vapor phase semiconductor reactants required for nanoscale wire growth may be produced by laser ablation of solid targets, vapor-phase molecular species, or the like. To create a single junction within a nanoscale wire, the addition of the first reactant may be stopped during growth, and then a second reactant may be introduced for the remainder of the synthesis. Repeated modulation of the reactants during growth may also be used, which may produce nanoscale wire superlattices. Different catalysts suitable for growth may be used, for example, a gold catalyst can be used in a wide-range of III-V and IV materials. Nearly monodisperse metal clusters or particles may be used to control the diameter, and, through growth time, the length various semiconductor nanoscale wires.

As another example, such methods may be used to create nanoscale wires having a multishell configuration. For example, by altering the synthetic conditions during growth, homogeneous reactant decomposition may occur on the surface of the nanoscale wire. Control of the synthetic conditions may lead to a shell forming on the surface of at least a portion of the nanoscale wire, and in some embodiments, the synthetic reaction conditions may be controlled to cause the formation of a thin, uniform shell, a shell having a thickness of one atomic layer, or less in some cases. In other embodiments, by modulating or altering the reactants during growth, more than one shell may be built up on the outer surface of the nanoscale wire. As one example, a silicon nanoscale wire core may be grown, and additional semiconductor materials may be deposited onto at least a portion of the surface, for example, a germanium shell, or a silicon shell doped with a dopant such as boron, or other dopants as described elsewhere in this application. The boundaries between the shells may be atomically abrupt, or may be graduated in some fashion, depending on how reactants such as, for example, silane, germane, or diborane are introduced into the laser catalytic growth system. Arbitrary sequences of Si, Ge, and alloy overlayers on both Si and Ge nanowire cores may also be prepared. Other factors may also contribute to the growing nanoscale wire, such as, for example, the reaction temperature, or the sample position within the furnace. By varying these parameters, the ratio of axial growth to radio growth may be controlled as desired.

The buffer gas may be any inert gas, for example, $N_2$ or a noble gas such as argon. In some embodiments, a mixture of $H_2$ and a buffer gas may be used to reduce undesired oxidation by residual oxygen gas.

A reactive gas used during the synthesis of the nanoscale wire may also be introduced when desired, for example, ammonia for semiconductors containing nitrogen, such as gallium nitride. Nanoscale wires may also be flexibly doped by introducing one or more dopants into the composite target, for example, a germanium alloy during n-type doping of InP. The doping concentration may be controlled by controlling the relative amount of doping element, for example, between 0% and about 10% or about 20%, introduced in the composite target.

Laser ablation may also be used to generate liquid nanoclusters that subsequently define the size and/or direct the growth direction of the nanoscale wires. The diameters of the resulting nanoscale wires may be determined by the size of the catalyst cluster or particle, which may be varied by controlling the growth conditions, such as the pressure, the temperature, the flow rate and the like. For example, lower pressure may produce nanoscale wires with smaller diameters in certain cases. Further diameter control may be performed by using uniform diameter catalytic clusters or particles.

If uniform diameter nanoclusters (e.g., less than 10% or less than 20% variation depending on the uniformity of the nanoclusters) are used as the catalytic cluster, nanoscale wires with uniform size (diameter) distribution can be produced in some embodiments, where the diameter of the nanoscale wires is determined by the size of the catalytic clusters. By controlling the growth time or the position of the sample within the reactor, nanoscale wires with different lengths and/or different shell thicknesses may be grown.

Nanoscale wires having uniform diameters or size distributions may be produced in embodiments where the diameter of the nanoscale wire is determined by the size of the catalytic cluster. For example, uniform diameter nanoclusters (for example, having a variation of less than about 10% or less than about 20% in the average diameter) may be used as the starting catalytic clusters.

The diameters of the resulting nanoscale wires may be determined by the size of the catalyst cluster, which in turn may be determined using routine experiments that vary the growth conditions, such as background pressure, temperature, flow rate of reactants, and the like. For example, lower pressure generally produces nanoscale wires with smaller diameters. Further diameter control may be achieved by using uniform diameter catalytic clusters.

The catalytic clusters or the vapor phase reactants may be produced by any suitable technique. For example, laser ablation techniques may be used to generate catalytic clusters or vapor phase reactant that may be used. Other techniques may also be contemplated, such as thermal evaporation techniques.

According to another aspect, semiconductor nanoscale wires such as those described herein can be used in a variety of electronic devices. Techniques for assembling one or more nanoscale wires on a surface, e.g., as part of an electronic device, are known to those of ordinary skill in the art, and include, but are not limited to, electric field alignment, fluid flow, surface regions that selectively attract nanoscale wires, biomolecular recognition, SAMs, micro-contact printing, chemically patterned surfaces, Langmuir-Blodgett techniques, or the like. Non-limiting examples of these and other techniques are disclosed in Ser. No. 10/196,337, entitled, "Nanoscale Wires and Related Devices," filed Jul. 16, 2002, published as Publication No. 2003/0089899 on May 15, 2003, incorporated herein by reference in its entirety.

For example, nanoscale wires such as those described herein may be used in a wide variety of devices. Such devices may include electrical devices, optical devices, optronic devices, spintronic devices, mechanical devices or any combination thereof, for example, optoelectronic devices, and electromechanical devices. Functional devices assembled from the nanoscale wires of the present invention may be used to produce various computer or device architectures. Non-limiting examples of these and other devices are disclosed in Ser. No. 10/196,337, entitled, "Nanoscale Wires and Related Devices," filed Jul. 16, 2002, published as Publication No. 2003/0089899 on May 15, 2003, incorporated herein by reference.

As mentioned, one aspect of the invention involves a sensor, which can be an electronic sensor, and a nanoscale wire able to detect the presence, or absence, of an analyte in a sample (e.g. a fluid sample) containing, or suspected of containing, an analyte. For example, the analyte may be present within a contained environment, as previously discussed. Nanoscale sensors of the invention may be used, for example, in chemical applications to detect pH or the presence of metal ions; in biological applications to detect a protein, nucleic acid (e.g. DNA, RNA, etc.), a sugar or carbohydrate, and/or metal ions; and in environmental applications to detect pH, metal ions, or other analytes of interest.

In one set of embodiments, one or more reaction entities may be used to determine the analyte. The term "reaction entity" refers to any entity that can interact with an analyte in such a manner to cause a detectable change in a property of a nanoscale wire (e.g., one acting as a transistor channel in a field effect transistor). The reaction entity may enhance the interaction between the nanoscale wire and the analyte, or generate a new chemical species that has a higher affinity to the nanoscale wire, or to enrich the analyte around the nanoscale wire. The reaction entity can comprise a binding partner to which the analyte binds. The reaction entity, when a binding partner, can comprise a specific binding partner of the analyte. For example, the reaction entity may be a nucleic acid, an antibody, a sugar, a carbohydrate or a protein. The reaction entity also may be a polymer, catalyst, or a quantum dot. A reaction entity that is a catalyst can catalyze a reaction involving the analyte, resulting in a product that causes a detectable change in the nanoscale wire, e.g. via binding to an auxiliary binding partner of the product electrically coupled to the nanoscale wire.

The term "binding partner" refers to a molecule that can undergo binding with a particular analyte, or "binding partner" thereof, and includes specific, semi-specific, and non-specific binding partners as known to those of ordinary skill in the art. For example, Protein A is usually regarded as a "non-specific" or semi-specific binder. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies specifically bind to their antigen, and the like. The binding may be by one or more of a variety of mechanisms including, but not limited to ionic interactions, and/or covalent interactions, and/or hydrophobic interactions, and/or van der Waals interactions, etc.

Certain embodiments of the present invention are generally directed to an article comprising a nanoscale wire and a detector constructed and arranged to determine a change in an electrical property of the nanoscale wire. The nanoscale wire may be, for example, acting as a gate in a field effect transistor. At least a portion of the nanoscale wire is addressable by a fluid containing, or suspected of containing, an analyte. The phrase "addressable by a fluid" is defined as the ability of the fluid to be positioned relative to the nanoscale wire so that an analyte suspected of being in the fluid is able to interact with the nanoscale wire. The fluid may be proximate to or in contact with the nanoscale wire.

The following definitions will aid in the understanding various aspects of the invention. However, all definitions as used herein are solely for the purposes of this application. These definitions should not necessarily be imputed to other commonly-owned applications, whether related or unrelated to this application.

Certain devices of the invention may include wires or other components of scale commensurate with nanometer-scale wires, which includes nanotubes and nanowires. In some embodiments, however, the invention comprises articles that may be greater than nanometer size (e.g., micrometer-sized). In all embodiments, specified widths can be smallest width (i.e. a width as specified where, at that location, the article can have a larger width in a different dimension), or largest width (i.e. where, at that location, the article's width is no wider than as specified, but can have a length that is greater).

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, for example, ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like.

As used herein, a "wire" generally refers to any material having a conductivity of or of similar magnitude to any semiconductor or any metal, and in some embodiments may be used to connect two electronic components such that they are in electrical communication with each other. For example, the terms "electrically conductive" or a "conductor" or an "electrical conductor" when used with reference to a "conducting" wire or a nanoscale wire, refers to the ability of that wire to pass charge. Typically, an electrically conductive nanoscale wire will have a resistivity comparable to that of metal or semiconductor materials, and in some cases, the electrically conductive nanoscale wire may have lower resistivities, for example, a resistivity lower than about $10^{-3}$ Ohm m, lower than about $10^{-4}$ Ohm m, or lower than about $10^{-6}$ Ohm m or $10^{-7}$ Ohm m.

A "nanoscale wire" (also known herein as a "nanoscopic-scale wire" or "nanoscale wire") generally is a wire, that at any point along its length, has at least one cross-sectional dimension and, in some embodiments, two orthogonal cross-sectional dimensions less than 5 micrometers, preferably less than 1 micrometer, preferably less than about 500 nm, preferably less than about 200 nm, more preferably less than about 150 nm, still more preferably less than about 100 nm, even more preferably less than about 70, still more preferably less than about 50 nm, even more preferably less than about 20 nm, still more preferably less than about 10 nm, and even less than about 5 nm. In other embodiments, the cross-sectional dimension can be less than 2 nm or 1 nm. In one set of embodiments, the nanoscale wire has at least one cross-sectional dimension ranging from 0.5 nm to 200 nm. In some cases, the nanoscale wire is electrically conductive.

In some embodiments, the nanoscale wire is cylindrical. In other embodiments, however, the nanoscale wire can be faceted, i.e., the nanoscale wire may have a polygonal cross-section. Where nanoscale wires are described having, for example, a core and a shell, the above dimensions generally relate to those of the core. The cross-section of a nanoscale wire may be of any arbitrary shape, including, but not limited to, circular, square, rectangular, annular, polygonal, or elliptical, and may be a regular or an irregular shape. The nanoscale wire may be solid or hollow.

Any nanoscale wire or other nanoscale object can be used in any of the embodiments described herein, including carbon nanotubes, graphene nanoribbons, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscale dimension, also can be used in some instances, e.g. inorganic structures such as main group and metal atom-based wire-like silicon, transition metal-containing wires, gallium arsenide, gallium nitride, indium phosphide, germanium, cadmium selenide structures. A wide variety of these and other nanoscale wires can be grown on and/or applied to surfaces in patterns useful for electronic devices in a manner similar to technique described herein involving nanoscale wires, without undue experimentation.

The nanoscale objects (e.g., nanoscale wires), in some cases, may be formed having dimensions of at least about 100 nm, at least about 300 nm, at least about 1 micrometer, at least about 3 micrometers, at least about 5 micrometers, or at least about 10 micrometers or about 20 micrometers in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

As used herein, a "nanotube" (e.g. a carbon nanotube) is a nanoscale wire that is hollow, or that has a hollowed-out core, including those nanotubes known to those of ordinary skill in the art. "Nanotube" is abbreviated herein as "NT." Nanotubes are used as one example of small wires for use in the invention and, in certain embodiments, devices of the invention include wires of scale commensurate with nanotubes.

A "nanowire" (e.g. comprising silicon or another semiconductor material) is a nanoscale wire that is generally a solid wire, and may be elongated in some cases. Preferably, a nanowire (which is abbreviated herein as "NW") is an elongated semiconductor, i.e., a nanoscale semiconductor. A "non-nanotube nanowire" is any nanowire that is not a nanotube. In one set of embodiments of the invention, a non-nanotube nanowire having an unmodified surface is used in any arrangement of the invention described herein in which a nanowire or nanotube can be used.

Many (but not all) nanoscale wires as used in accordance with the present invention are individual nanoscale wires. As used herein, "individual nanoscale wire" means a nanoscale wire free of contact with another nanoscale wire (but not excluding contact of a type that may be desired between individual nanoscale wires, e.g., as in a crossbar array). For example, an "individual" or a "free-standing" article may, at some point in its life, not be attached to another article, for example, with another nanoscale wire, or the free-standing article maybe in solution. This is in contrast to nanotubes produced primarily by laser vaporization techniques that produce materials formed as ropes having diameters of about 2 nm to about 50 nm or more and containing many individual nanotubes. This is also in contrast to conductive portions of articles which differ from surrounding material only by having been altered chemically or physically, in situ, i.e., where a portion of a uniform article is made different from its surroundings by selective doping, etching, etc. An "individual" or a "free-standing" article is one that can be (but need not be) removed from the location where it is made, as an individual article, and transported to a different location and combined with different components to make a functional device such as those described herein and those that would be contemplated by those of ordinary skill in the art upon reading this disclosure.

As used herein, an "elongated" article (e.g. a semiconductor or a section thereof) is an article for which, at any point along the longitudinal axis of the article, the ratio of the length of the article to the largest width at that point is greater than 2:1. This ratio is termed the "aspect ratio."

In some embodiments, at least a portion of a nano scale wire may be a bulk-doped semiconductor. As used herein, a "bulk-doped" article (e.g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles such as carbon nanotubes are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. In particular, in some embodiments, a bulk-doped semiconductor may comprise two or more bulk-doped regions. Thus, as used herein to describe nanoscale wires, "doped" refers to bulk-doped nanoscale wires, and, accordingly, a "doped nanoscopic (or nanoscale) wire" is a bulk-doped nanoscale wire. "Heavily doped" and "lightly doped" are terms the meanings of which are clearly understood by those of ordinary skill in the art. In some cases, one or more regions may comprise a single monolayer of atoms ("delta-doping"). In certain cases, the region may be less than a single monolayer thick (for example, if some of the atoms within the monolayer are absent). As a specific example, the regions may be arranged in a layered structure within the nanoscale wire, and one or more of the regions may be delta-doped or partially delta-doped.

As used herein, a "width" of an article is the distance of a straight line from a point on a perimeter of the article, through the center of the article, to another point on the perimeter of the article. As used herein, a "width" or a "cross-sectional dimension" at a point along a longitudinal axis of an article is the distance along a straight line that passes through the center of a cross-section of the article at that point and connects two points on the perimeter of the cross-section. The "cross-section" at a point along the longitudinal axis of the article is a plane at that point that crosses the article and is orthogonal to the longitudinal axis of the article. The "longitudinal axis" of an article is the axis along the largest dimension of the article. Similarly, a "longitudinal section" of an article is a portion of the article along the longitudinal axis of the article that can have any length greater than zero and less than or equal to the length of the article. Additionally, the "length" of an elongated article is a distance along the longitudinal axis from end to end of the article.

As used herein, a "cylindrical" article is an article having an exterior shaped like a cylinder, but does not define or reflect any properties regarding the interior of the article. In other words, a cylindrical article may have a solid interior or may have a hollowed-out interior. Generally, a cross-section of a cylindrical article appears to be circular or approximately circular, but other cross-sectional shapes are also possible, such as a hexagonal shape. The cross-section may have any arbitrary shape, including, but not limited to, square, rectangular, or elliptical. Regular and irregular shapes are also included.

As used herein, a first article (e.g., a nanoscale wire or larger-sized structure) "coupled" to a second article is disposed such that the first article either physically contacts the second article or is proximate enough to the second article to influence a property (e.g., an electrical property, an optical property, or a magnetic property) of the second article. The term "electrically coupled" when used with reference to a nanoscale wire and an analyte or another moiety such as a reaction entity, refers to an association between any of the analyte, other moiety, and the nanoscale wire such that electrons can move from one to the other, or in which a change in an electrical characteristic of one can be determined by the other. This may include electron flow between these entities, or a change in a state of charge, oxidation state, redox potential, and the like. As examples, electrical coupling can include direct covalent linkage between the analyte or other moiety and the nanoscale wire, indirect covalent coupling (e.g. via a linking entity), direct or indirect ionic bonding, or other types of bonding (e.g. hydrophobic bonding). In some cases, no actual bonding may be required and the analyte or other moiety may simply be contacted with the nanoscale wire surface. There also need not necessarily be any contact between the nanoscale wire and the analyte or other moiety, in embodiments where the nanoscale wire is sufficiently close to the analyte to permit electron tunneling or other field effects between the analyte and the nanoscale wire.

As used herein, an "array" of articles (e.g., nanoscale wires) comprises a plurality of the articles, for example, a series of aligned nanoscale wires, which may or may not be in contact with each other. As used herein, a "crossed array" or a "crossbar array" is an array where at least one of the articles contacts either another of the articles or a signal node (e.g., an electrode).

As used herein, a "semiconductor" is given its ordinary meaning in the art, i.e., an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, phosphorous, or compound semiconductors such as CdS. The semiconductor may be undoped or doped (e.g., p-type or n-type).

As used herein, a "single crystal" item (e.g., a semiconductor) is an item that has covalent bonding, ionic bonding, or a combination thereof throughout the item. Such a single crystal item may include defects in the crystal, but is distinguished from an item that includes one or more crystals, not ionically or covalently bonded, but merely in close proximity to one another.

The term "fluid" generally refers to a substance that tends to flow and to conform to the outline of its container. Typically, fluids are materials that are unable to withstand a static shear stress. When a shear stress is applied to a fluid, it experiences a continuing and permanent distortion. Typical fluids include liquids and gasses, but may also include free flowing solid particles, viscoelastic fluids, and the like.

The following documents are incorporated herein by reference: U.S. patent application Ser. No. 10/995,075, filed Nov. 22, 2004, entitled "Nanoscale Arrays, Robust Nanostructures, and Related Devices," by Whang, et al., published as U.S. Patent Application Publication No. 2005/0253137 on Nov. 17, 2005; International Patent Application No. PCT/US10/50199, filed Sep. 24, 2010, entitled "Bent Nanowires and Related Probing of Species," by Tian, et al., published as WO 2011/038228 on Mar. 31, 2011; U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; U.S. Pat. No. 7,129,554, issued Oct. 31, 2006, entitled "Nanosensors," by Lieber, et al.; and U.S. Pat. No. 7,301,199, issued Nov. 27, 2007, entitled "Nanoscale Wires and Related Devices," by Lieber, et al. In addition, U.S. Provisional Patent Application Ser. No. 61/495,919, filed Jun. 10, 2011, entitled "Nanoscale Wires, Nanoscale Wire FET Devices, and Nanotube-Electronic Hybrid Devices for Sensing and Other Applications," by Lieber, et al. is incorporated herein by reference.

The following examples are intended to illustrate certain embodiments of the present invention, but do not exemplify the full scope of the invention.

EXAMPLE 1

This example illustrates the development of intracellular electrical recording techniques capable of simultaneous multi-site recording with high spatial resolution and minimal invasiveness. This allows a network of electrogenic cells to be studied, for example, to understand signaling between the cells. In this example, a nanotube between the interior of living cell and the transistor channel of a field effect transistor (FET), such as a silicon nanowire FET, is demonstrated. A nanotube allows the cytosol of a cell to come into physical contact with the channel of the FET, thus allowing electrical coupling between the cell and FET to occur. The nanotube thus acts somewhat analogously to the gap junction in biological systems, through which various ions and molecules pass freely from one cell to another, allowing for communication between the cells. In some cases, the cytosol may enter the nanotube and act as the gate electrode to the FET. Thus, potential changes within the cytosol, e.g., due to action potentials in electrogenic cells, may be determined as a conductance change within the FET.

Unlike other potentiometric techniques, the nanotube can be miniaturized without substantial loss of signal amplitude. In this example, a full amplitude intracellular action potential from embryonic chicken cardiomyocyte cell was determined using a FET device having a single nanotube having an inner diameter of 50 nm and an outer diameter of 50 nm to 100 nm at the top, i.e., where the nanotube contacts the cytosol. These sizes were chosen in this example since decreasing nanotube inner diameters generally increases the electrical resistance of cytosol inside. For instance, a 1.5 micrometer long nanotube may have a limit on its inner diameter of about 2 nm at a bandwidth of 3 kHz. The nanotubes used in this example also illustrate minimal invasiveness and/or highly localized electrical detection. The detection is also generally repeatable, as illustrated by repeated intracellular recordings at the same position on a cardiomyocyte cell. In some cases, the FET channel may be chosen to have a diameter that is about the same as the I.D. of the nanotube at its tip. It was found that, in certain cases, increasing the width of the FET channel does not increase sensitivity of the device, but does increase the conductance background which might lead to higher noise levels and/or lower signal-to-noise ratios FETs generally output current or conductance change for an input of a change in the gate potential. Unlike other potentiometric methods such as metal electrodes or patch-clamp micropipettes, an FET sensor can be miniaturized without compromising signal amplitude or shape because the potential detected by an FET is not dependent on the impedance of the interface between the FET and the surrounding solution. Another advantage of FETs is that the output signal on an FET is current, which is not affected by capacitive coupling between different channels. Thus, multiple FETs can be used without cross-talk between the different FETs, which may happen in other potentiometric techniques where the different sensors are positioned too closely together. Cross-talk often occurs in other potentiometric techniques because the output is potential, rather than current. Accordingly, FET devices are not limited in terms of device density as are other potentiometric techniques, and thus, high spatial resolutions may be achieved in some cases, for example, using multiple nanotube FET devices. In some cases, simultaneous, multi-site intracellular electrical recordings with high spatial resolution may be achieved, as demonstrated by multiplexing recordings from chicken cardiomyocytes, in both single cell and larger networks of cells.

In biological systems, certain passages are created between cells and are commonly used for cell-to-cell communication. An example is a gap junction, which is formed from a protein. Gap junctions are often used to transmit action potentials in cardiac myocyte systems. Ions and/or small molecules are able to move through the gap junction between cells without significant external leakage, thereby allowing fast, efficient, and synchronizable coupling between cells. The devices used in this example are similar in concept, allowing coupling between a cell and an electronic device, thereby allowing similar fast, efficient, and/or synchronizable coupling between a cell and an electronic device.

To study the electrical behavior of a cell, in this example, the channel of the FET (connecting a source electrode to a drain electrode) is positioned to be in contact with the intracellular cytosol of the cell, but the electrodes themselves are not contacted with the cell, thereby minimizing the invasiveness of the FET. The FET in this example also allows for high spatial resolution multiplexing intracellular recording. However, instead of directly putting the FET channel inside the cell, a nanotube is used between the cell and the FET channel.

Figure 1B:
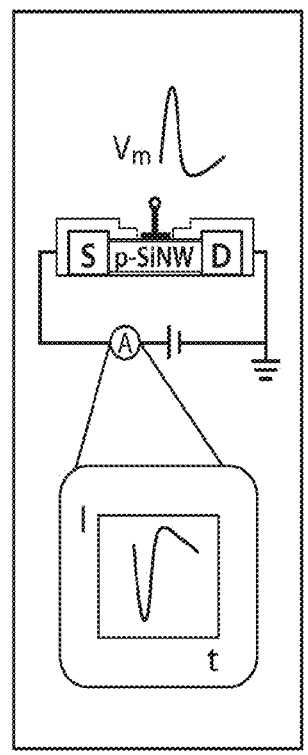

As FIG. 1A shows, nanotube 10 allows at least a portion of cytosol 15 of cell 20 to come into physical contact with a p-doped SiNW (silicon nanowire) 25 that acts as a transistor channel for FET 30 between source (S) electrode 35 and drain (D) electrode 37. When there is a change in the transmembrane potential ($V_m$) of the cell, such as during an action potential, the potential of the cytosol inside the nanotube may change accordingly, and thereby modulate the conductance of the p-SiNW FET, reflected in a change in current (I) when a constant voltage is applied between the source (S) and drain (D) electrodes. For a p-doped SiNW FET such as is used here, increasing the potential of the cytosol may cause a decrease in the conductance within the SiNW. Thus, the recorded signal will have a reversed polarity, compared to the actual potential of the action potential, as is illustrated in FIG. 1B.

To fabricate a nanotube between the interior of living cell and a SiNW FET, the nanotube is first synthesized on the SiNW FET, then the nanotube is inserted or otherwise internalized into a living cell. A nanotube-on-SiNW FET device was formed in this example by using a germanium nanowire (GeNW) that is grown as a "branch" on a SiNW, then used as a sacrificial template to prepare the nanotube.

FIG. 5 schematically shows the fabrication process. Briefly, after SiNW is dispersed on a substrate (FIG. 5A), a gold (Au) dot is prepared on top of the SiNW by e-beam lithography (EBL) and thermal evaporation (FIG. 5B). Then, a GeNW is grown using gold-catalyzed chemical vapor deposition (CVD) (FIG. 5C). Due to the presence of the gold dot on the surface of the SiNW, the GeNW grows as a heterobranch from the SiNW.

Next, source and drain metal contacts are defined or synthesized on the SiNW (FIG. 5D). In other embodiments, the gold dot and GeNW can be defined after the electrodes are fabricated instead of before, as the temperatures used during CVD growth of the GeNW are relatively low, and can be controlled such that the temperatures won't destroy or damage contact between the SiNW and metal electrodes. Other techniques may also be used in other embodiments to prepare a gold dot on the surface of the SiNW, for example, high-throughput methods like site-controlled chemical reduction, photolithography, or the like.

Next, atomic layer deposition (ALD) may be used to deposit $SiO_2$ onto the substrate (FIG. 5E). ALD may allow a uniform and conformal coating of $SiO_2$ on the substrate. The SiNW channel and the metal electrodes are covered by $SiO_2$, while the GeNW is also wrapped in $SiO_2$. Then, photoresist may be spin-coated thereon (FIG. 5F) and baked there. The thickness of the photoresist can be controlled to be smaller than the GeNW height, thereby allowing the topmost part of the GeNW/$SiO_2$ core/shell structure to protrude from the photoresist layer.

Buffered hydrofluoric acid (BHF) etching is then used (FIG. 5G) to remove the $SiO_2$ shell to expose the GeNW core. BHF etching is isotropic; thus, removal of $SiO_2$ proceeds along both the radial and axial directions. This may result in a generally tapering shape of the $SiO_2$ shell, e.g., such that it has a smaller thickness and outer diameter on the top, generally increasing downwards, e.g., to a constant value where the $SiO_2$ was not reached by BHF (and thus was not etched).

Figures 5G, 5H, 5I:
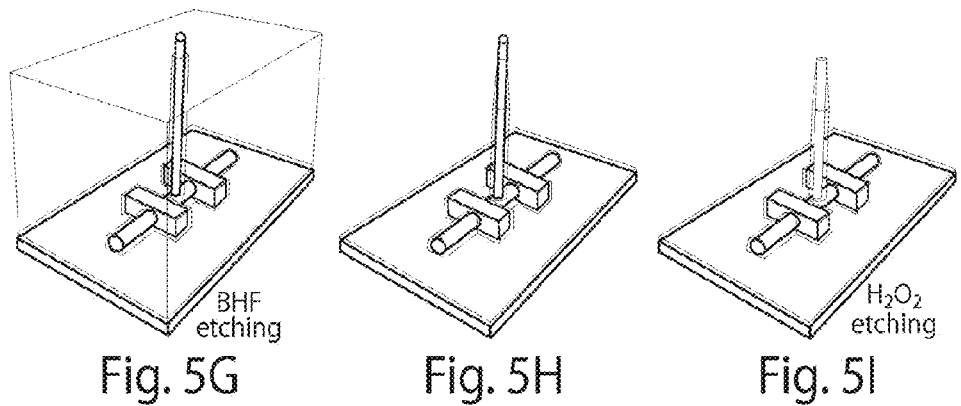

Next, hydrogen peroxide ($H_2O_2$) is used to etch the GeNW core, leaving a hollow tube structure standing on the SiNW channel (FIG. 5I). The GeNW will not be etched by H2O2 if without opening the SiO2 shell (even if the SiO2 thickness is only 5 nm), which indicates that the ALD SiO2 forms a conformal and leakage-free layer and there will be no leakage in the final nanotube too, which is necessary for the efficient coupling between the living cells and FET devices.

It should be understood that this description is by way of example only. In other embodiments, other techniques may be used to prepare a nanotube (or other nanoscale wire) of a FET, e.g., as a branched nanoscale structure. See, e.g., U.S. patent application Ser. No. 12/310,764, filed Mar. 6, 2009, entitled "Branched Nanoscale Wires," by Lieber, et al., published as U.S. Patent Application Publication No. 2011/0042641 on Feb. 24, 2011, incorporated herein by reference in its entirety. Other materials may also be used, instead of and/or in addition to silicon and germanium, e.g., as discussed herein, and/or other materials may also be used instead of and/or in addition to SiO2, such as $Al_2O_3$, $TiO_2$, $HfO_2$, Pt, Cu, Au, or the like. In addition, fabrication of nanowire FETs has been demonstrated using flexible or plastic substrates, etc., thus allowing conformal recording from tissues. See, e.g., U.S. patent application Ser. No. 10/995,075, filed Nov. 22, 2004, entitled "Nanoscale Arrays, Robust Nanostructures, and Related Devices," by Whang, et al., published as U.S. Patent Application Publication No. 2005/0253137 on Nov. 17, 2005, incorporated herein by reference in its entirety.

Figures 6A, 6B, 6C:
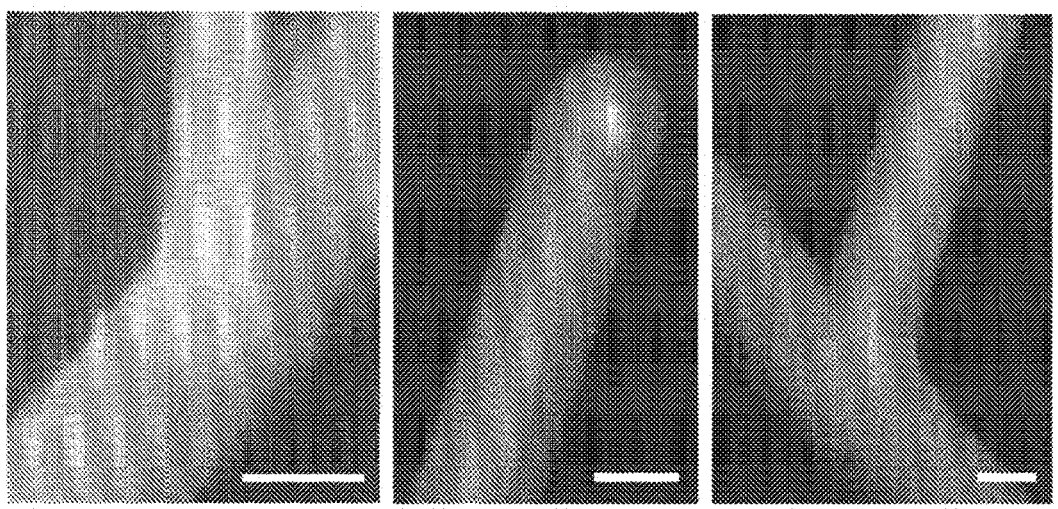
FIGS. 6A-6C are images of certain sensors in one set of embodiments.

FIGS. 1C-1E show scanning electron microscopy (SEM) images of an example nanotube-on-SiNW structures at different fabrication stages. The inset in FIG. 1C shows an image of a gold dot of about 80 nm size, 40 nm thick, on a SiNW having a diameter of about 100 nm. The scale bar in the inset is 100 nm. The size and/or thickness of the gold dot may be used to determine the diameter of the subsequent GeNW branch grown therefrom, and the inner diameter (I.D.) of the resulting nanotube. A gold dot such as the one illustrated here may be used to produce a GeNW having a diameter of about 50 nm. A typical image of a GeNW standing on a SiNW is shown in FIG. 1C. The scale bar in FIG. 1C is 200 nm. A magnified image of the bottom of the GeNW/SiNW interface part shown in FIG. 6A. The scale bar in FIG. 6A is 100 nm.

After CVD growth, the gold dot locates at the tip of the GeNW, which leaves a relatively clean and well-defined interface between the Ge and the Si at the bottom. As mentioned, the Ge may be coated with $SiO_2$, then removed to form a nanotube. The clean and well-defined interface, without metal between them, allows for any solution (e.g., cytosol) contained within the nanotube to directly contact the SiNW (with native SiO2), thereby allowing the SiNW to gate the solution effectively.

The length of the GeNW can be controlled by controlling CVD growth time. In the present example, the length of the GeNW was chosen to be between 2 micrometers and 3 micrometers, although other lengths could be chosen in other embodiments. The orientation of the crystal structure of the GeNWs is believed to be random, because of the un-epitaxial growth of the GeNW on the SiNW.

It should be noted that insertion of the nanotube into a living cell can be achieved without requiring the nanotube to be vertical or perpendicular to the surface of the cell. For example, a nanotube having any angle within 45° of vertical may be inserted into a living cell. As discussed below, phosopholipid modification may be used to facilitate insertion, where the nanotube is spontaneously inserted or uptaken by the cell due to the modifications. See also International Patent Application No. PCT/US10/50199, filed Sep. 24, 2010, entitled "Bent Nanowires and Related Probing of Species," by Tian, et al., published as WO 2011/038228 on Mar. 31, 2011, incorporated herein by reference in its entirety, for examples of other suitable nanotube modifications.

An image of a GeNW/SiNW heterostructure after the ALD $SiO_2$ coating has been deposited thereon is shown in FIG. 1D (magnified top and bottom images are also shown in FIGS. 6B and 6C, respectively). The scale bar in FIG. 1D is 200 nm, while the scale bars in FIGS. 6B and 6C are each 100 nm. The $SiO_2$ appears with darker contrast in the SEM image. The thickness of the $SiO_2$ layer was found to be about 50 nm, and the $SiO_2$ conformally covers both GeNW and SiNW. The image of the final structure of the $SiO_2$ nanotube on a SiNW can be seen in FIG. 1E, with the top and bottom magnified as shown in the respective insets in FIG. 1E (scale bars in FIG. 1E and in the FIG. 1E insets are each 200 nm). The upper inset shows a clear opening in the tip of the nanotube, and the core of the standing branch shows darker contrast which indicating the formation of a hollow tube structure, unlike in FIG. 1D. The darker contrast in the core goes to the bottom, which suggests removal of the GeNW core, thereby allowing exposure of the SiNW channel to cytosol or other fluids.

The nanotube appears to have a generally tapered shape, with thinner $SiO_2$ walls and a smaller outer diameter (O.D.) at its top. As discussed before, it is believed that this shape results from the etching of $SiO_2$ by the BHF solution in both the radial and axial directions. For a nanotube shown here with a 50 nm I.D. and a 50 nm thick $SiO_2$ wall, the very tip of the nanotube has an O.D. of about 50 nm to about 55 nm. As shown in FIG. 1E, the nanotube appears to linearly increases in size moving away from the tip. The top 40% of the nanotube appears to have an O.D. of less than 100 nm, and the maximum O.D. of the nanotube appears to be about 150 nm at roughly ⅔ of the way towards the base from the tip.

This tapered shape creates a smaller nanotube at the top part of the nanotube, which is the portion that is inserted or otherwise interfaces with cells. This tapered shape may also be useful in some embodiments to maintain the minimal invasiveness of living cells without having to decrease the $SiO_2$ thickness. The length of the final nanotube was about 1 micrometer to about 2.5 micrometers, depending on the length of the GeNW branch and the thickness of the resist used during $SiO_2$ BHF etching. Unless specifically mentioned, all the devices used in the following examples included nanotubes of 50 nm I. D., 50 nm thick $SiO_2$ walls, with a top I.D. of 50 nm, and a length of 1.5 micrometers, positioned on a p-doped SiNW having a diameter of 100 nm.

EXAMPLE 2

This example illustrates that the nanotube-on-SiNW FET devices described above are able to respond to fluids contained within the nanotube. For instance, if the nanotube is inserted into the cytosol of a cell while other portions of the device are exposed to the extracellular fluid outside of the cell (see FIG. 1A), the device will need to exhibit a suitable response to the cytosol, not the extracellular solution.

In this example, a response of the nanotube-on-SiNW FET device to an electrolyte in solution was studied, before and after removing the GeNW core. An FET without a nanotube but with a similar channel length was fabricated adjacent to a similar FET having a nanotube, and used as a control FET. This device is shown in FIG. 2. The nanotube FET is shown as S-D1, while the control FET is shown as S-D2.

Figure 2A:
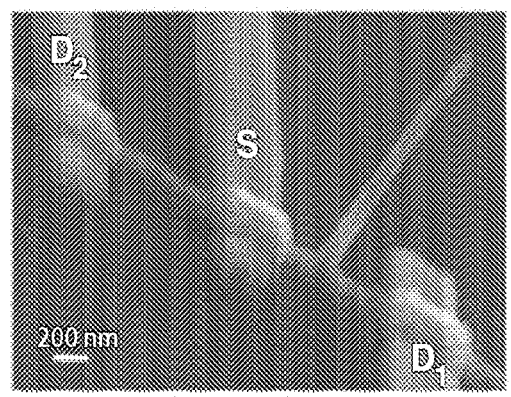
FIGS. 2A-2G illustrate electrical characterization and bandwidth analysis of certain sensors in another set of embodiments.
Figure 2B:
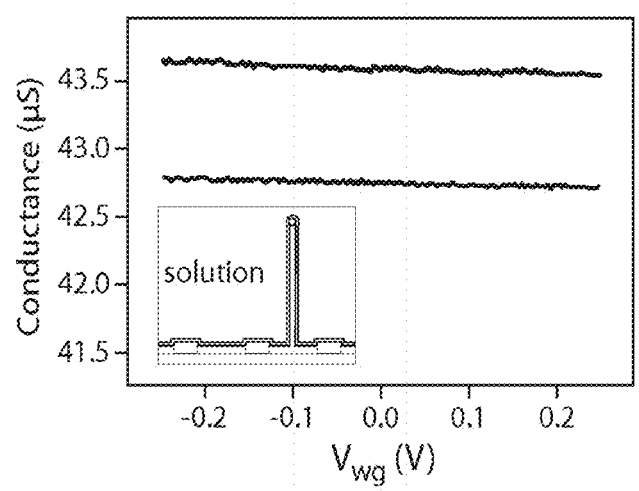

Gate curves from the two FETs before GeNW etching are shown in FIG. 2B. Both FETs showed small conductance changes of about −85 nS under a water gate potential $V_{wg}$ change of 0.5 V, which gives a transconductance of −170 nS/V. In particular, in this figure, both the control FET (upper trace) and the nanotube FET (lower trace) showed relatively level transconductance curves. The transconductance is defined as the conductance change of the FET per unit change of gate voltage. However, after removal of GeNW core and the nanotube formation, the nanotube FET showed a significantly increased transconductance of −4,530 nS/V, as the diagonal curve in FIG. 2C shows, while that of the control FET remains unchanged, as the level curve shows.

Before removing the GeNW, the nanotube FET (S-D1 in FIG. 2A) was gated by a solution surrounding the FET (see inset in FIG. 2B). The low, negligible transconductance under these conditions indicated relatively low sensitivity to the solution outside of the nanotube. The transconductance was found to be generally proportional to the capacitance between the gate electrode (i.e., the surrounding solution) and the FET channel. It is believed that the 50 nm $SiO_2$ layer between the solution and the SiNW significantly reduced the capacitance, and acts as a passivation layer that prevents the SiNW FET from substantially sensing any potential changes in the solution.

Figure 2C:
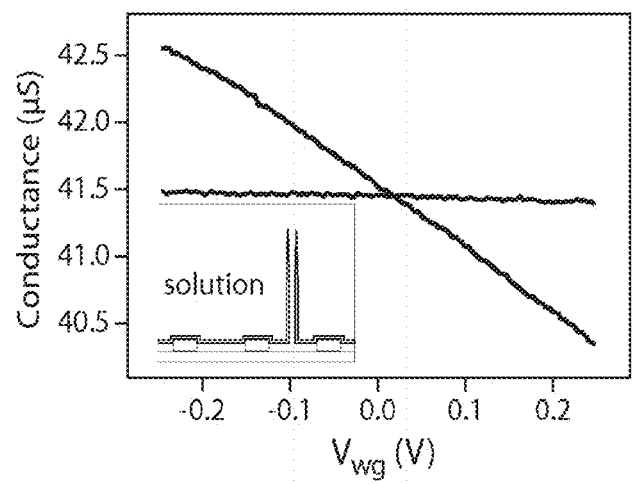

However, after GeNW removal, it is believed that the solution is able to at least partially fill in the nanotube (see inset in FIG. 2C). The significantly increased transconductance that was observed indicated the much higher sensitivity of the FET to the solution. This is consistent with the fact that there is likely only 1 nm to 2 nm of native oxide between the solution within the nanotube and the SiNW. The unchanged transconductance of the similarly positioned control FET shows that the increased transconductance of SD1 is likely due to nanotube formation (for example, rather than a product of a reaction between the $SiO_2$ and the etching solution). Thus, these results suggest that the nanotube-on-SiNW FET is able to respond to a fluid inside the nanotube, with relatively high sensitivity.

EXAMPLE 3

Figure 2D:
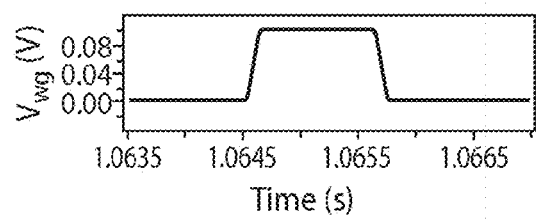

One important specification of the nanotube-on-SiNW FET is its bandwidth. If the resistance of the fluid inside the nanotube is too high, there may be a delay in response of the change in potential at the bottom of the nanotube following a change in the transmembrane potential, which may cause distortion of the resulting signal. To determine the bandwidth, a voltage pulse ($V_{wg}$, water gate voltage) was applied and the conductance change of the FET in response to the pulse was determined (FIG. 2D).

The amplitude of the voltage pulses was 0.1 V and the rise time was decreased from 50 ms to 0.1 ms. The duration of the voltage pulse was ten times the duration of the rise time. FIG. 2D shows the 0.1 ms rise time pulse. The conductance change of a nanotube-on-SiNW FET in response to this pulse is shown by trace 40 in FIG. 2E, and that of a control FET without nanotube is shown by the black trace in FIG. 7B. The amplitude of the applied pulses was kept at 0.1 V, and the duration was kept as ten times of the rise time. The conductance changes were measured as an average during 0.2 ms to 0.5 ms after the pulse was started. The two spikes at the ramp-up and ramp-down of the pulse are from the capacitive charging of the metal electrodes (passivated by the $SiO_2$ layer), i.e., from the metal electrodes used to connect the FET to outer electronics. However, this effect may be minimized if the potential change is localized to the interior of the nanotube and is not coupled to the outer metal electrodes.

Figure 2E:
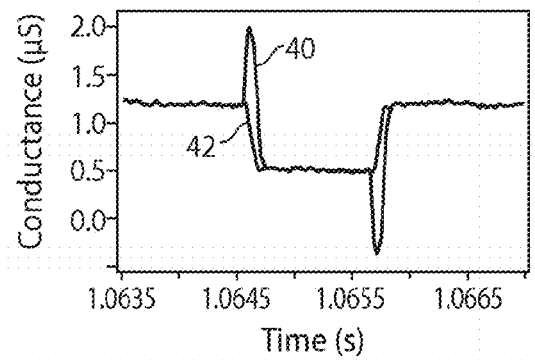
Figure 2F:
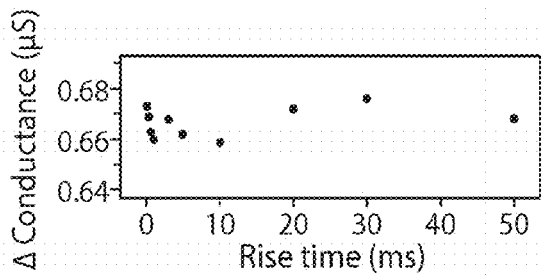
Figure 7A:
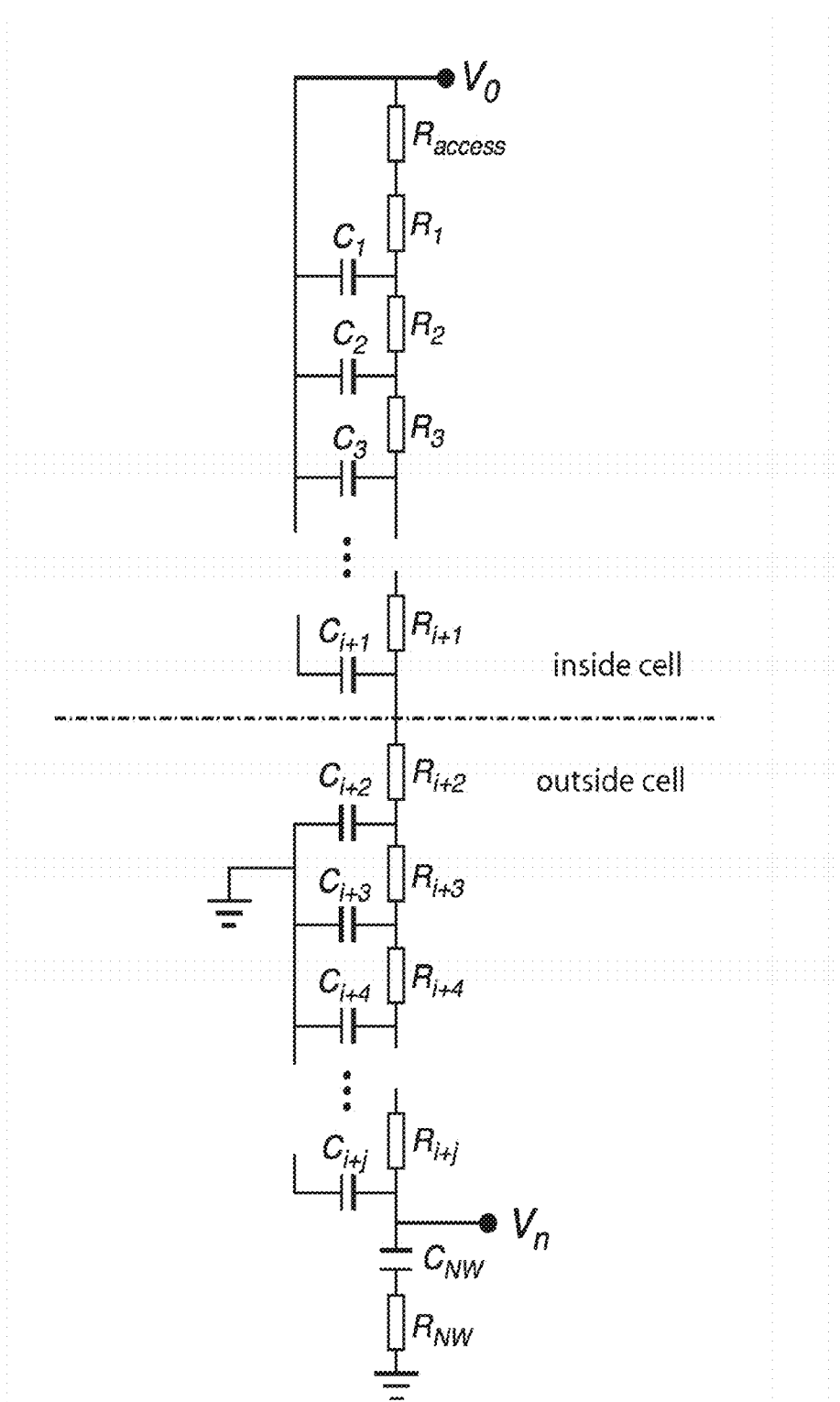
FIGS. 7A-7C illustrate data demonstrating certain electrical characteristics of a sensor in one embodiment of the invention.
Figure 7B:
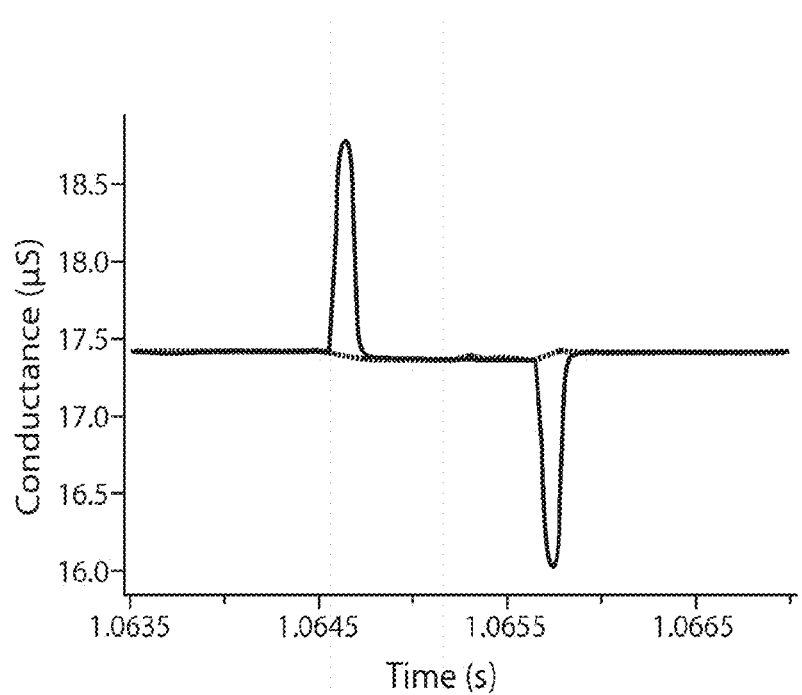

The nanotube FET showed a decrease in conductance in response to the positive $V_{wg}$ pulse in FIG. 2F, while the control FET showed negligible conductance change in FIG. 7B, consistent with the results shown in FIG. 2C. Subtracting the two spikes from the conductance trace as discussed below allows the pure field-effect response of the nanotube-on-SiNW FET device to be obtained. This is the conductance change to the localized potential change. This response is shown in FIG. 2E as trace 42. The conductance of the FET reached a constant steady value about the same time the water gate potential reached 0.1 V. This shows that the potential at the nanotube bottom/SiNW surface is able to follow the potential outside of the nanotube, without any substantial or detectable delay. In FIG. 2F, the SiO2 thickness was kept the same as the inner diameter of the nanotube, 50 nm, and the nanotube length was held at 1.5 micrometers. In the inset, the calculated change of the potential at the nanotube end, $V_n$, was normalized with $V_0$, in response to a transmembrane potential change of $V_0$.

Further, the conductance change of the FET appears to show no attenuation for a small rise time pulse, such as one with a duration of 0.1 ms, as compared to a longer pulse with rise time of 50 ms, as shown in FIG. 2E. The absence of attenuation or delay shows that this nanotube-on-SiNW FET device here has adequate bandwidth to record a signal having a time scale of 0.1 ms.

With respect to the determination of the pure field-effect response of the nanotube-on-SiNW FET, because the water gate potential change is global and fast, there may be capacitive coupling current between the bulk solution and the metal electrodes that were passivated by ALD $SiO_2$. This capacitive coupling current from the electrodes can appear as +/− spikes in the conductance measurements during ramp-up or ramp-down. To remove these spikes, a control device without a $SiO_2$ nanotube was fabricated and measured together with the nanotube-on-SiNW FET device (black trace in FIG. 7B).

For the control FET, because the SiNW responds to the water gate potential linearly and instantaneously without delay, the baseline conductance (i.e., before and after a pulse) and the steady state conductance after the water gate potential reached steady state during the pulse can be used to reconstruct the idealized SiNW field-effect response (dashed trace in FIG. 7B, in response to a water gate potential pulse of 0.1 V, rise time of 0.1 ms, and duration of 1 ms). Subtracting this idealized field-effect response from the original conductance change of the control FET produces a pure capacitive coupling signal for the control FET. Scaling this capacitive coupling signal with the ratio of the electrode area between the nanotube FET and control FET produces the capacitive coupling signal of the nanotube device. This can then be subtracted from the original conductance change of the nanotube device to produce a pure field-effect response, as is shown by trace 42 in FIG. 2E. Notice that this calculation has no fitting parameters, and the capacitive coupling spikes can be completely removed.

EXAMPLE 4

Due to the bandwidth limit of the measurement setup, the bandwidth of the nanotube-on-SiNW FET devices discussed above was calculated under intracellular recording conditions. This calculation used 1-dimensional finite element method based on a transmission line model.

The $SiO_2$ nanotube is modeled as shown in FIG. 7A. Resistors $R_1, \ldots, R_{i+j}$ model the distributed resistance of the fluid inside the nanotube. Capacitors $C_1, \ldots, C_{i+j}$ model the distributed capacitance between the inside and outside of the nanotube. $R_{access}$ is the access resistance from the internal fluid to the opening of the nanotube. $V_0$ is the intracellular potential of the cell. Outside of the cell, the fluid outside the nanotube is grounded by the reference electrode. $V_n$ is the potential at the end of the nanotube (i.e., at the SiNW surface). $C_{NW}$ is the gate capacitance of the SiNW, and $R_{NW}$ is the resistance of the SiNW.

The cell electrical potential signal propagates from the opening of the nanotube to the end of nanotube (where it couples to the FET channel) through the electrically conductive fluid. During the propagation, the potential signal also couples to the fluid outside of the nanotube by capacitive coupling across the $SiO_2$ nanotube wall. This can be modeled as a classical transmission line problem. Using the Ohm's law and capacitive coupling at any point of the nanotube, the propagation of electrical potential signal can be described by the following partial differential equations:

$$\begin{cases} -\dfrac{\partial V_{in}}{\partial z} = \rho_R I \\ -\dfrac{\partial I}{\partial z} = \rho_C \dfrac{\partial (V_{in} - V_{out})}{\partial t} \end{cases} \quad [1]$$

Here, $V_{in}$, $V_{out}$, $\rho_R$, $\rho_C$, I, z, t are the potential inside the nanotube, the potential outside the tube, the linear resistivity of solution inside the nanotube (i.e., resistance per unit length), the capacitance of the nanotube wall per unit length, the current, the distance from the nanotube opening, and time, respectively. These equations can be further simplified to produce:

$$\dfrac{\partial^2 V_{in}}{\partial z^2} = \rho_R \rho_C \left( \dfrac{\partial V_{in}}{\partial t} - \dfrac{\partial V_{out}}{\partial t} \right) \quad [2]$$

$\rho_R$ can be estimated from the solution bulk resistivity $\rho_{Bulk}$ as $\rho_R = 4\pi \rho_{Bulk}/d^2$, and $\rho_C$ can be calculated from the geometry of the nanotube by a cylindrical capacitor model as $\rho_C = 2\pi\epsilon\epsilon_0/\ln((d+2l)/d)$. Here d, l, $\epsilon$ and $\epsilon_0$ are the nanotube inner diameter, the $SiO_2$ thickness, the relative dielectric constant of $SiO_2$, and the vacuum dielectric constant, respectively. The double layer capacitance of the fluid can also be considered, although its contribution is negligible due to the small Debye length arising from the high ionic strength under physiological conditions.

The potential at the end of the nanotube was evaluated as a function of time under cell potential changes, based on Equation (2), using 1-dimensional finite element methods (written in Mathematica, Wolfram Research, Inc.). The boundary conditions for the simulation were as follows: Outside the cell membrane, $V_{out}$ was fixed by the reference electrode; inside the cell membrane, $V_{out}$ equaled to the intracellular potential of the cell; ⅓ of the nanotube was inside the cell; and the gate capacitance, $C_{NW}$, of the SiNW was approximated as a parallel plate capacitor.

The bandwidth is evaluated by using a fast ramp of the cell potential from 0 to a steady-state value $V_0$, and simulating the corresponding change of the potential at the end of the nanotube $V_n$ versus time. The effective bandwidth, BW, was estimated by:

$$BW \approx 0.35/\tau \quad [3]$$

where $\tau$ is the time it takes for $V_n$ to change from 10% to 90% of $V_0$.

Figure 2G:
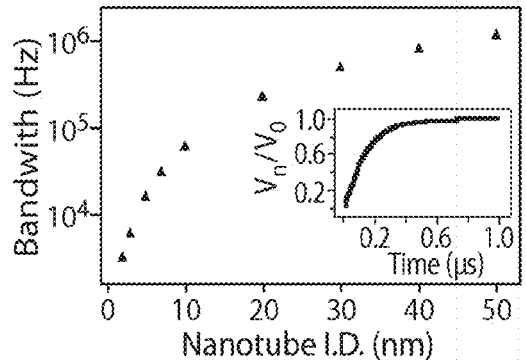

Thus, for a nanotube with an inner diameter and a $SiO_2$ thickness of 50 nm, a length of 1.5 micrometers, the calculated normalized change of $V_n$, the potential at the nanotube bottom/SiNW surface, is shown in the inset of FIG. 2G. The graph includes an extremely steep ramp-up of the transmembrane potential from 0 to a steady value of V0, with a 0.1 ns rise time. The calculation estimates a bandwidth as high as 1.19 MHz for the present nanotube dimension.

The high bandwidth benefits from the small capacitance of the nanotube-on-SiNW FET device. For example, although the fluid (having physiological resistivity) inside the nanotube gives a total resistance as high as about 760 megohms (MΩ), the capacitance of the nanotube was only about 0.3 fF, which assured relatively high bandwidth regardless of the high resistance of the fluid. However, biological processes, such as action potentials, are typically slower, e.g., normally in the kHz range, or less. Thus, these calculations show that the nanotube-on-SiNW FET devices used here will have adequate bandwidth to record such biological processes without significant distortion.

Figure 7C:
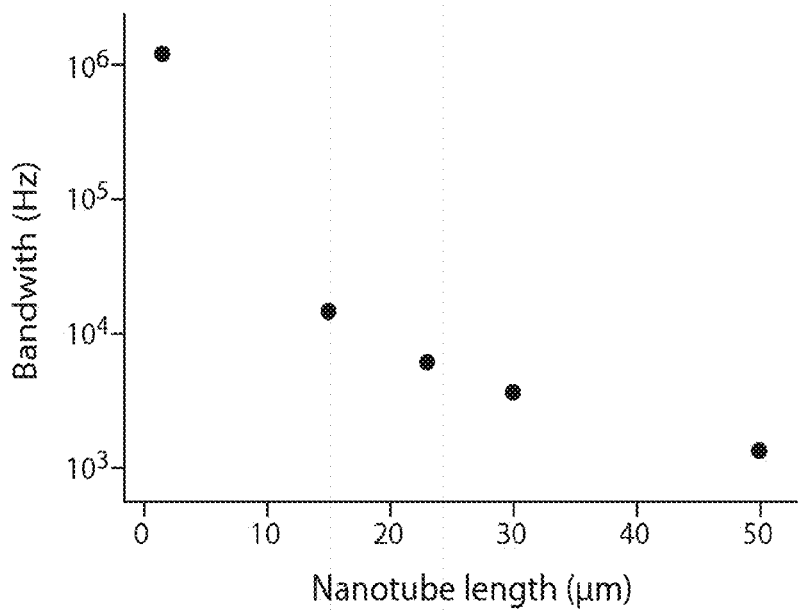

The dependence of bandwidth on nanotube size was also calculated as is shown in FIG. 2G. The $SiO_2$ thickness was kept equal to the nanotube inner diameter. From this data, the bandwidth was calculated to reach 3 kHz when the nanotube inner diameter was decreased to ~2 nm. This was used as the size limit for using the nanotube-on-SiNW devices in intracellular action potential recordings in cells. This diameter is also about the size range of a protein, and thus is expected to represent almost no invasiveness to cell. Furthermore, the small size of the nanotube may facilitate the intracellular electrical recording from small features within the cells, such as neuron dendrites and spines. In addition, it should be noted that bandwidth may also be a function of the length of the nanotube, as the data shown in FIG. 7C illustrate. These simulations were run using a nanotube inner diameter of 50 nm and a $SiO_2$ thickness of 50 nm. Other parameters in these simulations were the same as those described above.

EXAMPLE 5

In this example, spontaneously firing embryonic chicken cardiomyocyte cells were studied to demonstrate the intracellular electrical recording of action potentials with nanotube-on-SiNW FET devices similar to those discussed above. The nanotube of the device was modified with phospholipid bilayers to facilitate the internalization of nanotube into the cell. See FIG. 8A, which shows a false-color fluorescence image of a device after phospholipid modification. The phospholipid DMPC was doped with 1% nitrobenzoxadiazole dye-labeled lipids and imaged through a 510/21 band-pass filter. The bright fluorescence image showed that the supported lipid bilayer is successfully formed. See also International Patent Application No. PCT/US10/50199, filed Sep. 24, 2010, entitled "Bent Nanowires and Related Probing of Species," by Tian, et al., published as WO 2011/038228 on Mar. 31, 2011, incorporated herein by reference in its entirety.

Embryonic chicken cardiomyocytes were cultured using established protocols on thin PDMS films. The devices were incubated with lipid vesicles of 1,2-dimyristoyl-snglycero-3-phosphocholine (DMPC, Avanti Polar Lipids Inc.) containing 1% 1-myristoyl-2-{12-[(7-nitro-2-1,3-benzoxadi-azol-4-yl)amino]dodecanoyl}-sn-glycero-3-phosphocholine (NBD-lipid, Avanti Polar Lipids Inc.) which acted as a fluorescent reporter to form supported lipid bilayers on device including nanotube surfaces.

Cell recording measurements were carried out in a tyrode solution (pH~7.3) with a 100 mV DC source voltage at 37° C. The current was amplified with a custom-built multi-channel current preamplifier, filtered with a 6 kHz low pass filter (CyberAmp 380), and digitized at 50-250 kHz sampling rate (Axon Digi1440A). Ag/AgCl reference electrodes were used as reference electrode to hold constant the extracellular solution potential in all recording experiments. The PDMS/cell sheets were manipulated using a glass micropipette to control the relative position between the cells and the nanotubes.

Measurements was carried out using a custom-built PDMS/cell manipulation apparatus, although direct culture of cells on the nanotube-on-SiNW FET device is also possible. The chicken cardiomyocyte cells were cultured on thin PDMS sheets. The PDMS/cell sheet was positioned on the device with the cells side facing down. A micromanipulator was used to position cell on nanotube-on-SiNW FET device and move the cell along the z direction to enable intracellular coupling.

Figure 3A:
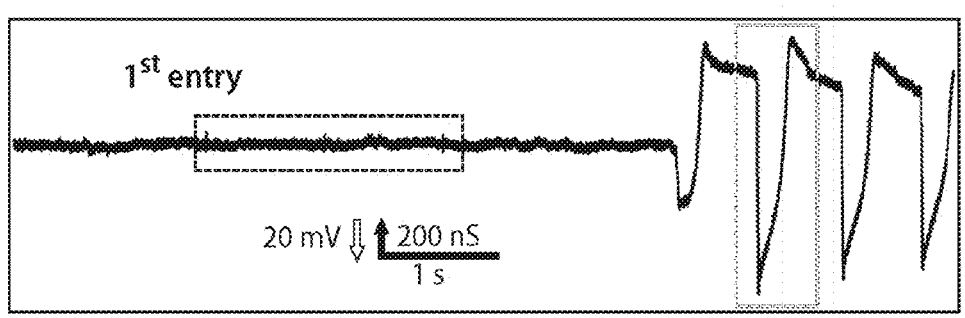
FIGS. 3A-3E illustrate monitoring of cells using certain sensors in accordance with some embodiments of the invention.
Figure 3B:
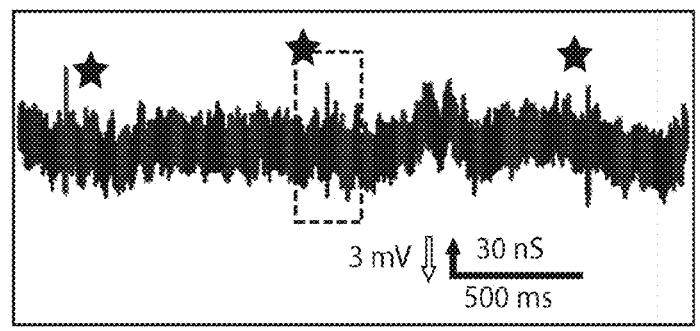
Figure 3C:
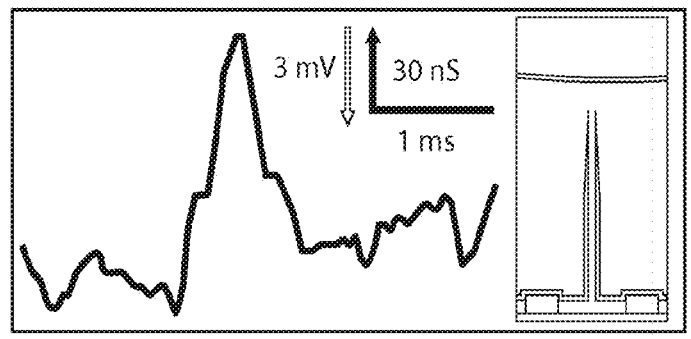
Figure 3D:
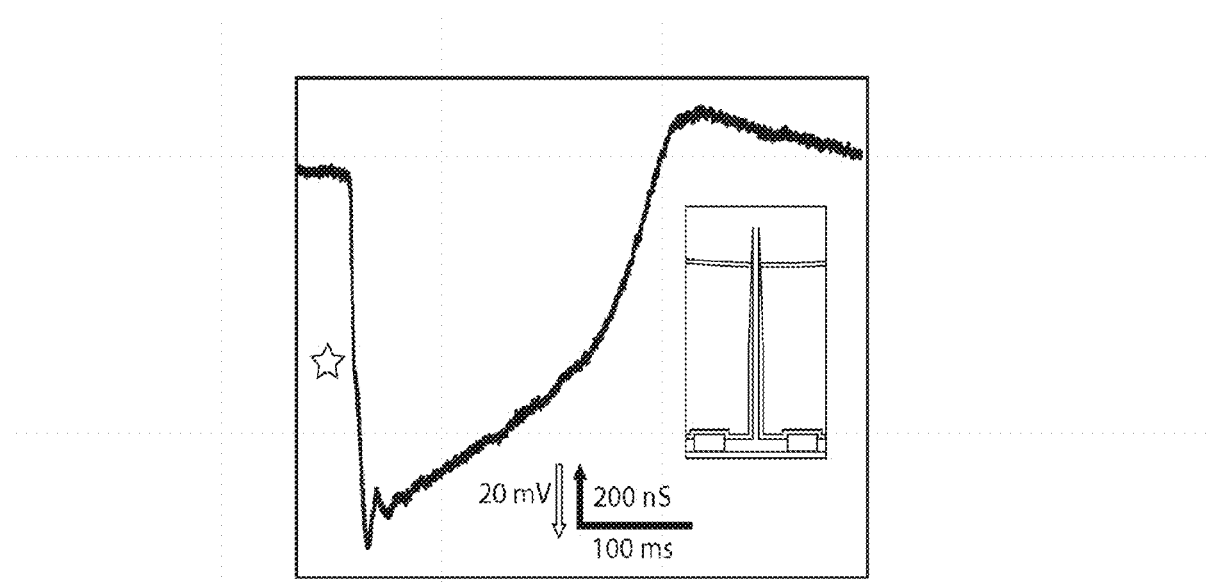

Steps of 0.2 micrometers were used in the manipulator when cells were near the device, with one minute delays between movements. Internalization of nanotubes into the cells happened spontaneously, without application of any external forces, suggesting that the phospholipid bilayers facilitated spontaneous insertion, instead of mechanical action. Before the nanotube entered the cell, it was filled with extracellular media and the underlying SiNW FET was used to record extracellular potential changes as a baseline. After entering the cell, intracellular cytosol was expected to replace the fluid within the nanotube, so that the signal recorded by the SiNW FET would reflect intracellular potential changes. Due to the small size of the nanotube, the extracellular media within the nanotube was expected to represent only negligible toxicity to the cell. A typical trace corresponding to the internalization of the nanotube into a cell (a spontaneously firing embryonic chicken cardiomyocyte cell) is shown in FIG. 3A. This trace, coincident with the beating of the cell with a frequency of about 1 Hz, showed extracellular-like biphasic spikes with magnitude of 5 mV to 8 mV, duration of 1 ms to 2 ms in the early part of the trace, then larger peaks of 80 mV to 100 mV, about 200 ms duration, along with a baseline shift of about −35 mV. FIG. 3B shows a magnified trace of the area in the black dashed rectangle in FIG. 3A. The extracellular signals are marked with stars. FIG. 3C shows a magnified trace of the peak marked by the dashed rectangle in FIG. 3B. FIG. 3D shows a magnified trace of the peak in the dashed rectangle in FIG. 3A.

These peaks had the shape and features of a typical intracellular action potential of a cardiomyocyte cell, including fast depolarization at the beginning of the peak, a plateau, fast repolarization, and hyperpolarization. The shape of these signals, especially that of the fast depolarization phase, was consistent with the larger bandwidth calculated above. The baseline shift is also consistent with the resting potential difference between the outside and inside the cell. The recorded intracellular action potential appeared to have a high signal-to-noise ratio. As seen from a magnified peaks in FIG. 3D, finer features like the occurrence of the inward $Ca^{2+}$ current following the inward $Na^+$ current during the fast depolarization phase, as marked by the star, could also be observed.

Figure 3E:
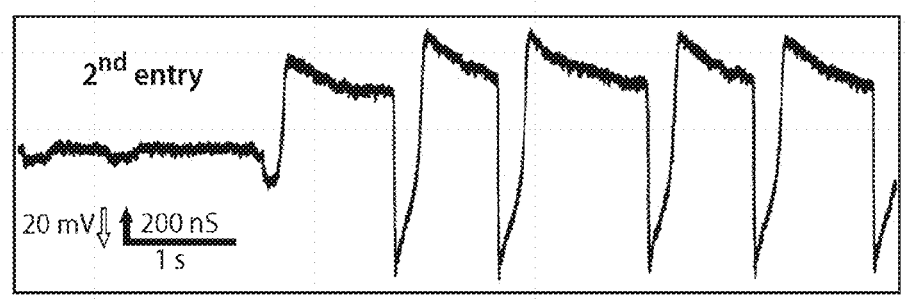

The nanotube could be retracted and internalized at essentially the same position of the cell, as is shown in FIG. 3E. However, different from the first entry in FIG. 3A, the second entry recorded more intermediate peaks. These intermediate peaks had similar polarity and durations, but smaller amplitudes, than the intracellular action potential. This intermediate state appeared to be random. Without wishing to be bound by any theory, it is believed that these intermediate peaks represent a state where the nanotube was tightly sealed to the cell membrane, without actually penetrating to the interior of the cell, and/or during the insertion process before the formation of tight electrical sealing between cell membrane and nanotube. As FIG. 3E shows, this process cloud be repeated multiple times (5 times shown here), without observable changes in cell behavior. This not only suggests minimal invasiveness of intracellular recording with the nanotube-on-SiNW FET device, but also demonstrates reliability and robustness.

Figure 8B:
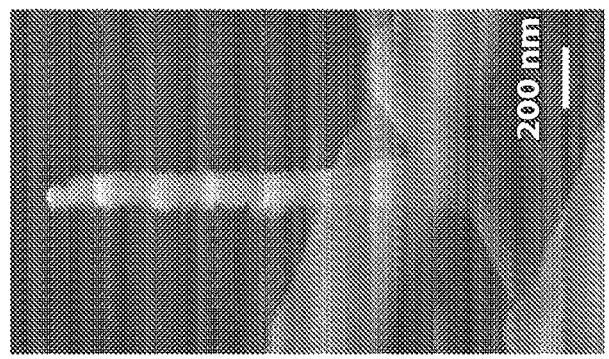
FIGS. 8A-8B are images of sensors in certain embodiments of the invention.
Figure 8A:
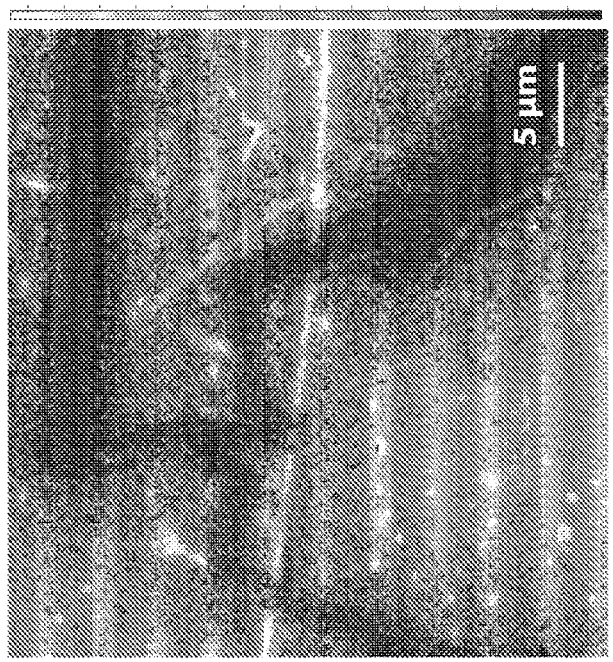

An SEM image of the nanotube-on-SiNW FET device after measurements is shown in FIG. 8B. Upon exiting, it appears that some residue from the cell remained on the top of the nanotube. However, if left within the cell, intracellular recordings could be made for fairly long times, while dislodgement ultimately occurred due to the beating motion of the cells.

EXAMPLE 6

Large area arrays of FETs with high device density, including arrays of SiNW FETs, have been discussed in the past. Thus, in combination with the systems and methods described herein, large area multi-site intracellular electrical recordings, simultaneously with high spatial resolution, can also be performed. An example of multiple nanotube-on-SiNW FET devices on a single SiNW is discussed with reference to FIG. 4. In this example, multiplexing capability is demonstrated using two experiments having different length scale.

The first experiment is shown in FIGS. 4A and 4B. Two nanotube-on-SiNW FET devices (separated by a distance of about 20 micrometers) were coupled to a single cardiomyocyte cell. FIG. 4A shows a differential interference contrast microscopy (DIC) image of two nanotube-on-SiNW FET devices coupled to a single cardiomyocyte cell, with the cell boundary marked by the dashed line. Representative traces of the recorded intracellular action potential signals using these FET devices are shown in FIG. 4B. The signals from these two FETs were near simultaneous, with a slight timing difference due to the small distance between them.

Figure 4D:
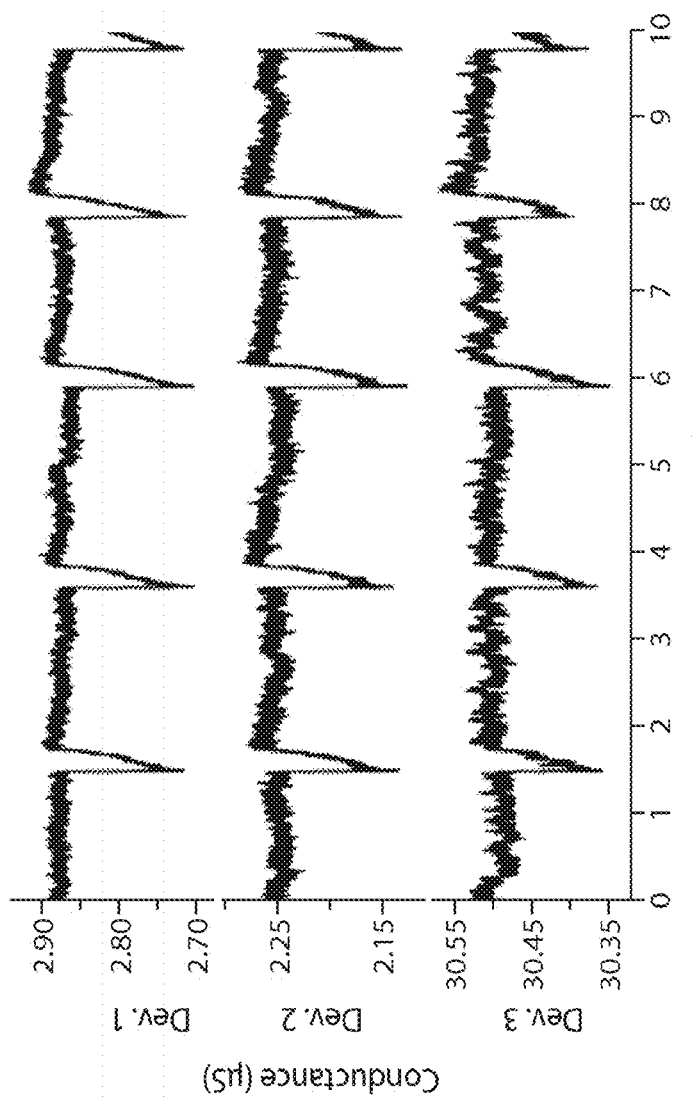
Figure 4C:
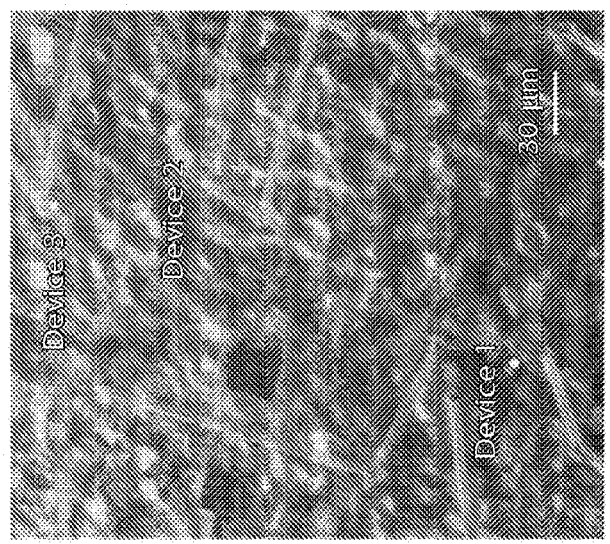

FIGS. 4C and 4F show multiplexing recording of three FET devices from a cardiac cellular network of cells. Each FET device monitored a different cell. FIG. 4C shows a DIC image of the three nanotube-on-SiNW FET devices coupled to a cardiac cellular network, while FIG. 4D shows representative traces the simultaneously recorded intracellular action potential signals from these three devices. The cells on the three FETs beat at the same phase, and the devices gave coincident intracellular action potential signals from the three cells. Cross correlation analysis on the signals demonstrates that the action potential got to device 3 first, passed by device 2, and reached device 1.

Figure 9B:
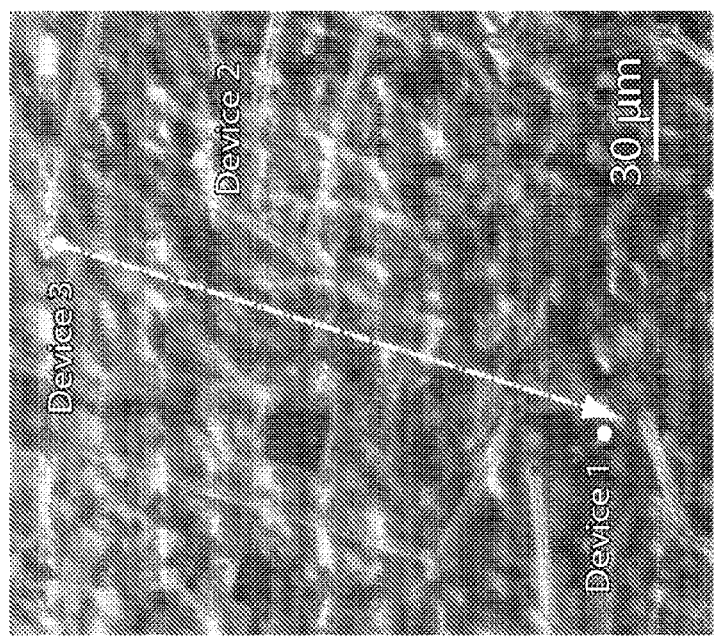
FIGS. 9A-9C illustrate the use of a plurality of sensors used in accordance with some embodiments of the invention.

To differentiate the timing sequence of the action potential signals along the three devices in FIG. 4C, cross-correlation analysis was performed. The fast rising edge of the recorded signal was precisely marked the beginning of the action potential. The total width of the signal was relatively long (about 200 ms), such that the slow transient tail was prone to fluctuations introduced by noises, leading to larger errors in the correlation results. Accordingly, only the fast transient peak of the signals was used in this analysis. The signals were first filtered through a lowpass filter with a cut-off frequency of 400 Hz. The first derivatives, which identify the position and width of the fast transient peak, were then extracted and inputted into the built-in correlation function of Igor Pro (WaveMetrics, Inc.) to calculate the time difference $\Delta t$ between different devices, one for each incidence of the action potential firing. All of the $\Delta t$ values of the 75 recorded signals were then assembled to determine the propagation sequence of action potentials through the three devices, as is shown in FIG. 9C. In this figure, the left part are timing offset results, plotted for each action potential peak. The right part is a histogram of this. $\Delta t_{1,2}$, $\Delta t_{1,3}$, and $\Delta t_{2,3}$ refers to the timing offset between signals from device 1 and 2, 1 and 3, 2 and 3 respectively. The distribution of the timing offset from all device pairs was mainly negative, demonstrating that the signal from device 1 lagged that from devices 2 and 3, and the signal from device 2 lagged the signal from device 3.

Figure 9A:
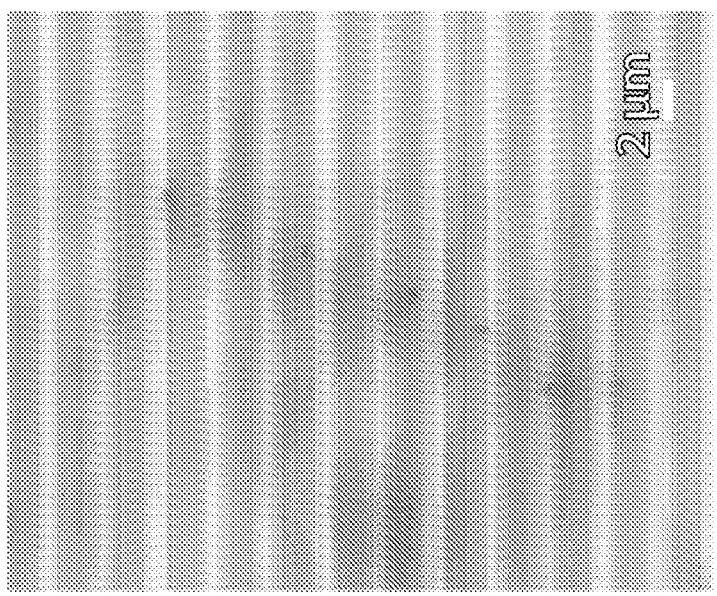
Figure 9C:
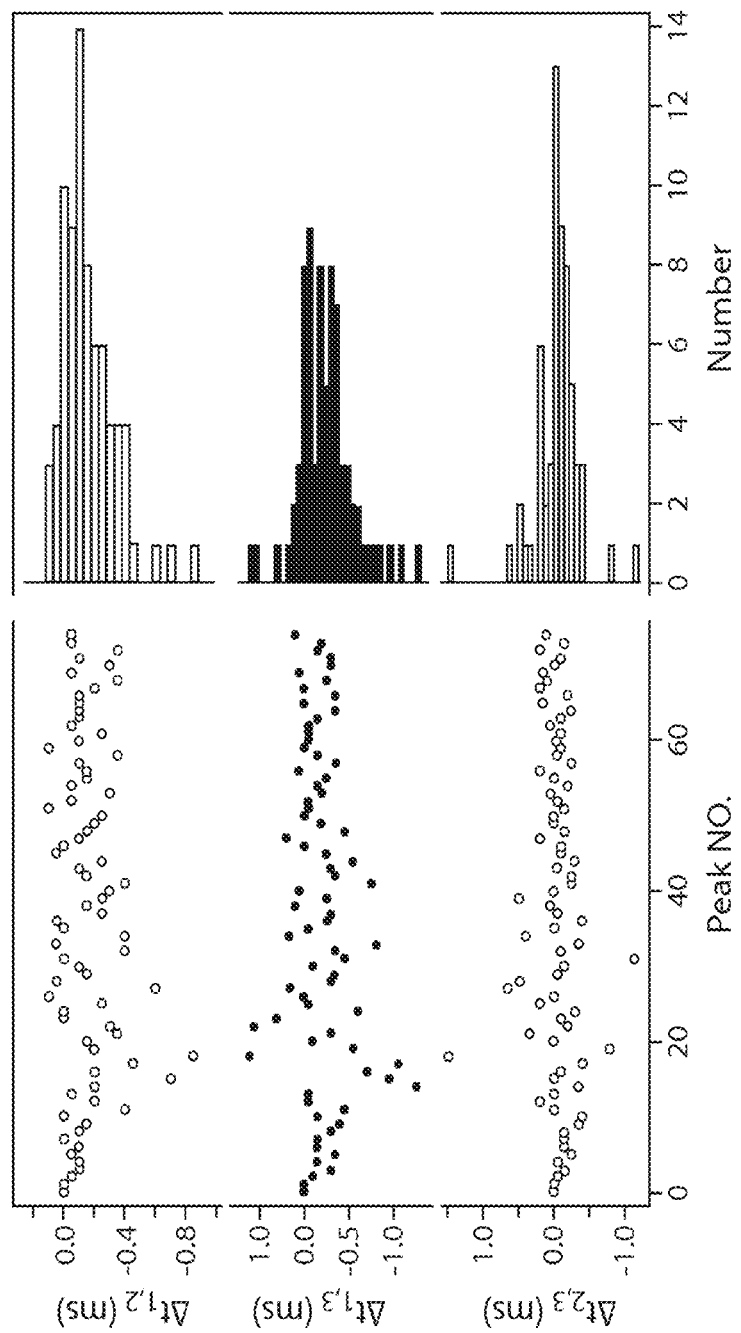

FIG. 9A is a bright-field optical image of the multiple devices made on a single SiNW. The focus plane is above the substrate surface and on the tip of the branches, which are shown as the black spots in the image. The electrodes images were blurred since they were not located in the focal plane. Because the $SiO_2$ nanotubes were invisible under bright-field optical microscope, the image shown here actually shows the devices before Ge is etching away, in order to visualize the branches. FIG. 9B shows a DIC image of the three nanotube-on-SiNW FET devices with beating chicken cardiomyocytes. The dashed arrow marks the sequence of the action potential passing through the three devices.

EXAMPLE 7

This example demonstrates certain techniques for nanowire synthesis as used in the examples discussed above. Single crystal p-doped silicon nanowires (p-SiNWs) were synthesized using a nanocluster catalyzed vapor-liquid-solid (VLS) process. See, e.g., U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; and U.S. Pat. No. 7,301,199, issued Nov. 27, 2007, entitled "Nanoscale Wires and Related Devices," by Lieber, et al., each incorporated herein by reference in its entirety. Briefly, 100 nm diameter gold nanoparticles (Ted Pella) were dispersed on $SiO_2$/Si growth substrates (Nova Electronic Materials), and growth was carried out at a total pressure of 25 torr, a temperature of 450° C. to 460° C., using $SiH_4$ (2.5 sccm), $B_2H_6$ (3 sccm, 100 ppm in He) and Ar carrier (10 sccm) for 20 min to 30 min.

Single crystal germanium nanowire (GeNW) branches were also synthesized by the Au nanocluster catalyzed VLS process. The 100 nm diameter p-SiNWs grown as mentioned above were deposited from isopropanol dispersion onto silicon chips with 100 nm thermal $SiO_2$ and 200nm $Si_3N_4$ on the surface (Nova Electronic Materials). A 300 nm thick poly(methylmethacrylate) (PMMA, Microchem Corp., Newton, Mass.) layer was spin coated on the chips and baked at 180° C. for 10 min, and 80 nm size Au dots with 40 nm thickness were patterned exactly on the top of the SiNWs by e-beam lithography (EBL, JEOL JSM-7000F) and thermal evaporation (Sharon). The chip was then treated with chemical vapor deposition for GeNW branches growth. The growth started with a nucleating step at 310° C., with a total pressure of 100 torr, using $GeH_4$ (10 sccm, 10% in $H_2$), and $H_2$ carrier (200 sccm) for 5 min. Then the temperature was decreased to 290° C. with other parameters held constant for ~20 min of elongation. This two-step growth produced relatively uniform 50 nm GeNW branches on SiNW backbones with minimal overcoating on both branches and backbones.

A schematic diagram of device fabrication is shown in FIG. 5. After GeNW branches were grown, a ~2 micrometer thick copolymer MMA (8.5) EL 11 (Microchem Corp., Newton, Mass.) layer followed by a 500 nm thick PMMA layer was spin-coated on the chip and baked at 180° C. for 10 min. Ti/Pd/Ti or Cr/Pd/Cr (1.5 nm/120 nm/10 nm) metal source and drain contacts were defined on SiNWs at the two sides of the GeNW branches through EBL and thermal evaporation. Critical point drying (Tousimis, Auto Samdri 815 Series A) was used during the lift-off and rinse step to avoid collapsing of the GeNW branches. Atomic layer deposition (ALD, Savannah-S200, Cambridge NanoTech) was used to deposit SiO2 on the chip using trimethylaluminum ($Me_3Al$, TMA) and tris(tert-butoxy)silanol [$(ButO)_3SiOH$] precursor at 250° C. Each deposition cycle include a 0.015 s TMA vapor pulse, a 5 s purge of 7 sccm $N_2$, and four 0.2 s pulses of silanol, with each of them followed by a 5 s $N_2$ purge. Each cycle produced another deposition of SiO2 about 1.5 nm (with one atomic layer of $Al_2O_3$). After $SiO_2$ deposition, the chip was kept in the chamber at 250° C., and a 15 min annealing step with multiple cycles of 0.015 s water vapor pulses followed by 5 s $N_2$ purge were performed.

To remove the Ge, a photoresist (Shipley S18-series, Shipley Company, Marlborough, Mass., diluted with thinner-P, Rohm and Haas, Philadelphia, Pa., as necessary) of thickness 1 micrometer to 2.5 micrometers (which was smaller than the GeNWs height) was spin-coated and baked at 115° C. for 5 min. The topmost part of the GeNW/$SiO_2$ core/shell structure protruded from the top of the photoresist. Buffered hydrofluoric acid (Buffer HF Improved, Transene) etching was used to remove the $SiO_2$ shell of the protruding portion and expose the Ge (20~25 s for 50 nm ALD SiO2). After resist lift-off, hydrogen peroxide ($H_2O_2$, 30%, Sigma) was used to etch away Ge under 50° C. for 45 min to 60 min.

A polydimethylsiloxane (PDMS) sheet with a window of 15 mm×10 mm×2 mm was put on the device chip. Phosphate buffered saline (PBS) was added to the window and an Ag/AgCl electrode was inserted into it. The water gate measurement was carried out by sweeping the voltage on the Ag/AgCl electrode. Water gate potential pulses were also applied through Ag/AgCl electrode to the bulk fluid.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A field effect transistor, comprising:
   a source electrode;
   a drain electrode;
   a transistor channel electrically connecting the source electrode to the drain electrode wherein the transistor channel comprises a nanoscale wire; and
   a nanotube positioned such that one end of the nanotube physically contacts a side of the transistor channel.

2. The field effect transistor of claim 1, wherein the nanotube contains a liquid.

3. The field effect transistor of claim 1, wherein the nanotube comprises an oxide.

4. The field effect transistor of claim 1, wherein the nanotube comprises a metal.

5. The field effect transistor of claim 1, wherein the nanotube is substantially nonconductive.

6. The field effect transistor of claim 1, wherein the nanotube has an inner diameter of less than about 5 micrometers.

7. The field effect transistor of claim 1, wherein the nanotube has a length of at least about 50 nm.

8. The field effect transistor of claim 1, wherein the nanotube has a length of at least about 1 micrometer.

9. The field effect transistor of claim 1, wherein the transistor channel is positioned substantially perpendicularly relative to the nanotube.

10. The field effect transistor of claim 1, wherein the transistor channel comprises a semiconductor.

11. The field effect transistor of claim 1, wherein the transistor channel is a solid nanowire.

12. The field effect transistor of claim 1, wherein the transistor channel has an average cross-sectional diameter of less than about 200 nm.

13. The field effect transistor of claim 1, wherein the transistor channel further comprises a coating.

14. A sensor, comprising:
    a substrate comprising a plurality of field effect transistors, at least some of which are the field effect transistors comprising a source electrode, a drain electrode, a transistor channel electrically connecting the source electrode to the drain electrode wherein the transistor channel comprises a nanoscale wire, and a nanotube positioned such that one end of the nanotube physically contacts a side of the transistor channel.

15. A method of determining an electrical property of a cell, comprising:
    inserting a fluidic channel into an interior of a cell, wherein the fluidic channel is in electrical communication with a portion of a gate of a field effect transistor and the gate is external of the cell, and wherein the fluidic channel is a nanotube; and
    determining an electrical property of the cell.

* * * * *

UNITED STATES PATENT AND TRADEMARK OFFICE
CERTIFICATE OF CORRECTION

PATENT NO. : 9,595,685 B2
APPLICATION NO. : 14/124816
DATED : March 14, 2017
INVENTOR(S) : Charles M. Lieber et al.

Page 1 of 1

It is certified that error appears in the above-identified patent and that said Letters Patent is hereby corrected as shown below:

In the Specification

Please replace the paragraph at Column 1, Line 24, with the following paragraph:
--This invention was made with government support under grant OD003900 awarded by the National Institutes of Health (NIH). The government has certain rights to this invention.--

Signed and Sealed this
Fifth Day of May, 2020

Andrei Iancu
*Director of the United States Patent and Trademark Office*